(12) United States Patent
Kast et al.

(10) Patent No.: US 7,364,741 B1
(45) Date of Patent: Apr. 29, 2008

(54) PEPTIDES OF HUMAN PAPILLOMA VIRUS FOR USE IN HUMAN T CELL RESPONSE INDUCING COMPOSITIONS

(75) Inventors: Wybe Martin Kast, Leiden (NL); Cornelis Joseph Maria Melief, Heemstede (NL); Alessandro D. Sette, La Jolla, CA (US); John C. Sidney, La Jolla, CA (US)

(73) Assignee: Pharmexa Inc., San Diego, CA (US)

( * ) Notice: Subject to any disclaimer, the term of this patent is extended or adjusted under 35 U.S.C. 154(b) by 0 days.

(21) Appl. No.: 08/170,344

(22) PCT Filed: May 4, 1993

(86) PCT No.: PCT/NL93/00093

§ 371 (c)(1),
(2), (4) Date: Mar. 30, 1994

(87) PCT Pub. No.: WO93/22338

PCT Pub. Date: Nov. 11, 1993

(30) Foreign Application Priority Data

| May 5, 1992 | (EP) | 92201252 |
| Dec. 10, 1992 | (EP) | 92203870 |
| Feb. 1, 1993 | (EP) | 93200243 |
| Mar. 5, 1993 | (EP) | 93200621 |

(51) Int. Cl.
*A61K 38/00* (2006.01)
*A61K 39/00* (2006.01)
*A61K 39/12* (2006.01)
*C07K 16/00* (2006.01)
*C07K 17/00* (2006.01)
*C07K 5/00* (2006.01)
*A01N 37/18* (2006.01)

(52) U.S. Cl. .............. 424/186.1; 424/184.1; 424/185.1; 424/204.1; 424/277.1; 530/300; 530/327; 530/328; 514/2

(58) Field of Classification Search .............. 530/300, 530/328, 327; 424/184.1, 204.1, 185.1, 186.1, 424/277.1; 514/2
See application file for complete search history.

(56) References Cited

U.S. PATENT DOCUMENTS

| 4,777,239 | A | * | 10/1988 | Schoolnik et al. | 530/326 |
| 5,415,995 | A | * | 5/1995 | Schoolnik et al. | 435/7.1 |
| 5,550,214 | A | * | 8/1996 | Eberlein et al. | 530/328 |
| 5,662,907 | A | * | 9/1997 | Kubo et al. | 424/185.1 |
| 5,679,509 | A | * | 10/1997 | Wheeler et al. | 435/5 |
| 5,686,068 | A | * | 11/1997 | Melief et al. | 424/93.71 |
| 5,932,412 | A | * | 8/1999 | Dillner et al. | 435/5 |
| 6,013,258 | A | * | 1/2000 | Urban et al. | 424/186.1 |
| 6,037,135 | A | * | 3/2000 | Kubo et al. | 435/7.24 |
| 6,147,187 | A | * | 11/2000 | Melief et al. | 530/327 |
| 6,183,745 | B1 | * | 2/2001 | Tindle et al. | 424/185.1 |
| 6,183,746 | B1 | * | 2/2001 | Urban et al. | 424/186.1 |
| 6,218,363 | B1 | * | 4/2001 | Baserga et al. | 514/15 |
| 6,242,176 | B1 | * | 6/2001 | Kast et al. | 435/5 |
| 6,419,931 | B1 | * | 7/2002 | Vitiello et al. | 424/201.1 |
| 6,548,299 | B1 | * | 4/2003 | Pykett et al. | 435/377 |
| 6,582,704 | B2 | * | 6/2003 | Urban et al. | 424/204.1 |
| 6,620,510 | B1 | * | 9/2003 | Taguchi et al. | 428/413 |
| 6,783,763 | B1 | * | 8/2004 | Choppin et al. | 424/204.1 |
| 6,797,491 | B2 | * | 9/2004 | Neefe et al. | 435/69.1 |
| 6,838,084 | B1 | * | 1/2005 | Jochmus et al. | 424/204.1 |
| 6,861,234 | B1 | * | 3/2005 | Simard et al. | 435/29 |
| 7,026,443 | B1 | * | 4/2006 | Sette et al. | 530/300 |
| 2002/0110566 | A1 | * | 8/2002 | Neefe et al. | 424/204.1 |
| 2003/0099634 | A1 | * | 5/2003 | Vitiello et al. | 424/130.1 |
| 2003/0170268 | A1 | * | 9/2003 | Neefe et al. | 424/201.1 |
| 2003/0175285 | A1 | * | 9/2003 | Klinguer-Hamour et al. | 424/185.1 |
| 2004/0091479 | A1 | * | 5/2004 | Nieland et al. | 424/144.1 |
| 2004/0106551 | A1 | * | 6/2004 | Khleif et al. | 514/12 |
| 2004/0141081 | A1 | * | 7/2004 | Morrison et al. | 348/333.01 |
| 2004/0147044 | A1 | * | 7/2004 | Mittelman et al. | 436/518 |
| 2004/0170644 | A1 | * | 9/2004 | Mailere et al. | 424/186.1 |
| 2004/0235741 | A1 | * | 11/2004 | Neefe et al. | 514/12 |
| 2004/0258708 | A1 | * | 12/2004 | Jochmus et al. | 424/186.1 |
| 2005/0033025 | A1 | * | 2/2005 | Choppin et al. | 530/350 |
| 2005/0048467 | A1 | * | 3/2005 | Sastry et al. | 435/5 |
| 2005/0100928 | A1 | * | 5/2005 | Hedley et al. | 435/6 |
| 2005/0130920 | A1 | * | 6/2005 | Simard et al. | 514/44 |
| 2005/0142541 | A1 | * | 6/2005 | Lu et al. | 435/5 |

(Continued)

FOREIGN PATENT DOCUMENTS

EP       0257754      *  3/1988

(Continued)

OTHER PUBLICATIONS

Matlashewski et al. 1986. The Expression of Human Papillomavirus type 18 E6 . . . J. Gen Viral 67:1909-16.*

(Continued)

*Primary Examiner*—Nita Minnifield
(74) *Attorney, Agent, or Firm*—Sterne, Kessler, Goldstein & Fox P.L.L.C.

(57) ABSTRACT

A peptide comprising an amino acid sequence derived from a human papilloma virus (HPV) protein, wherein said amino acid sequence has the ability to bind to a human Major Histocompatibility Complex Class I molecule. Its use in prophylactic or therapeutic treatment of cervical carcinoma and other HPV-related diseases.

12 Claims, 3 Drawing Sheets

U.S. PATENT DOCUMENTS

2005/0181458 A1* 8/2005 Harding et al. .............. 435/7.2
2006/0079453 A1* 4/2006 Sidney et al. ................. 514/12
2006/0094649 A1* 5/2006 Keogh et al. ................. 514/12

FOREIGN PATENT DOCUMENTS

| EP | 0375555 | | 6/1990 |
| --- | --- | --- | --- |
| EP | 0456197 | | 11/1991 |
| EP | 0593754 | B1 * | 4/1994 |
| WO | WO 9205248 | | 4/1992 |
| WO | WO 93/22338 | A1 * | 11/1993 |

OTHER PUBLICATIONS

Kast et al. 1991. In vivo efficacy of virus-derived peptide . . . Immunol. Letters. 30:229-232.*
Kast. et al. 1991. Protection against lethal Sendai virus infection by . . . PNAS. 88:2283-2287.*
Bowie et al. 1990. Science 247:1306-1310.*
Houghten et al. 1986. Vaccines 86 pp. 21-25.*
Kast et al, J. Immunology, 1994, 152:3904-3912.*
Burger et al, J. National Cancer Institute, 1996 88/19:1361-1368.*
Rudolf et al, Clinical Cancer Research, Mar. 2001, 7:788s-795s.*
Feltkamp et al, Eur. J. Immunology, 1993, 23:2242-2249.*
Zehbe et al, Cancer Research, 1998, 58:829-833.*
Watts et al, Int. J. Cancer, 2002, 97:868-874.*
Kennedy et al, J. Virology, Apr. 1991, 65/4:2093-2097.*
Tan et al, Cancer Research, 1995, 55:4599-4605.*
Dillner, Int. J. Cacner, 1990, 46:703-711.*
Seedorf et al, Virology, 1985, 145:181-185.*
Selvey et al, J. Virological Methods, 1992, 37:119-127.*
Tindle et al, PNAS, USA, 1991, 88/13:5887-5891.*
Altmann et al, Eur. J. Cancer, 1992, 28(2/3):326-333.*
Comerford et al, J. Virology, Sep. 1991, 65/9:4681-4690.*
Gariglio et al, Archives of Medical Research, 1998, 29/4:279-284.*
Hoppe-Seyler et al, Molecular Carcinogenesis, 1994, 10:134-141.*
Azoury-Ziadeh et al, Viral Immunol., 1999, 12/4:297-312.*
Stauss et al, PNAS, USA, 1992, 89/17:7871-7875.*
Stanley, Current Opinion in Molecular Therapeutics, 2002, 4/1:15-22.*
Welters et al, Cancer Research, 2003, 63:636-641.*
de Jong et al, Cancer Research, 2004, 64:5449-5455.*
de Jong et al, Cancer Research, 2002, 62:472-479.*
Lehtinen et al, Am. J. Obsete. Gynecol., 2003, 188:49-55.*
Lowy et al, PNAS, USA, 1994, 91:2436-2440.*
Breitburd et al, Seminars in Cancer Biology, 1999, 9:431-445.*
Altmann et al "Definition of immunogenic determinants of the human papillomavirus type 16 nucleoprotein E7"; European Journal of Cancer, vol. 28, No. 2/3, Feb. 1992, pp. 326-333.
Tindle et al "A 'public' T-helper epitope of the E7 transforming protein . . . " Proc. Natl Acad. Sci. USA. vol. 88, No. 13, Jul. 1991, pp. 5887-5891.
Comerford et al "Identification of T- and B-epitopes of the E-7 protein of human papillomavirus type 16", Journal of Virology, vol. 65, No. 9, Sep. 1991, pp. 4681-4690.
Stauss et al "Induction of cytotoxic T lymphocytes with peptides in vitro: Identification of candidate T-cell . . . ", Proc. Natl. Acad. Sci. USA, vol. 89, No. 17, Sep. 1, 1992, Washington US pp. 7871-7875.

* cited by examiner

PEPTIDES OF HUMAN PAPILLOMA VIRUS FOR USE IN HUMAN T CELL RESPONSE INDUCING COMPOSITIONS

FIELD OF THE INVENTION

The invention is concerned with novel peptides derived from Human Papilloma Virus proteins and their use in pharmaceutical compositions for a prophylactic or therapeutic treatment of human individuals against Human Papilloma Virus-related diseases such as cervical cancer.

BACKGROUND OF THE INVENTION

Human Papilloma Viruses (HPVs) are implicated in the etiology of cervical cancer, the fifth most common cancer worldwide and the second cause of cancer-related death in women. If also other HPV-related cancers are taken into account, up to 10% of the worldwide mortality due to cancer is linked to HPVs. HPVs are double stranded circular DNA viruses of about 8 kilobases. Until now more than 60 genotypes have been described of which several are associated with cancer.

HPV-DNA can be found in cervical dysplastic lesions and in cervical carcinomas in which the percentage of HPV positivity increases up to 99% when the lesions progress towards malignancy. The most important HPV types associated with cervical carcinoma are HPV16 and 18 of which HPV16 alone accounts for more than 50% of the HPV positive cervical carcinomas.

The DNAs of several HPVs have been sequenced. The DNA open reading frames can be divided into early regions (E) and late regions (L). The E regions are coding for proteins needed for virus replication and transformation. The L regions encode viral capsid proteins. The E6 and E7 proteins are involved in the pathogenesis of HPV-induced abnormal cell proliferation and these genes are expressed in tissue or tumor cells obtained from cervical cancers associated with HPV infection.

In addition, the E6 and E7 genes of HPV16 and HPV18 are capable of inducing epithelial cell transformation in the cell culture without the presence of other HPV genes indicating that at least part of the stimulation of cell proliferation caused by HPV infection is due to the E6 and E7 viral proteins.

Cytotoxic T lymphocytes (CTL) are of crucial importance in the resistance against virus infections and the immune surveillance against virus-induced tumors (reviewed by Kast and Melief, 1991). CTL specific for viruses or virus-induced tumors recognize short viral protein-derived peptides, of about 9 amino acids in length, that are bound to the antigen presenting groove of major histocompatibility complex (MHC) class I molecules (reviewed by Kast and Melief, 1991). Recently, in several virus systems vaccination with peptides recognized by antigen-specific CTL was shown to prevent lethal virus infections and to delay tumor growth in mice (reviewed by Kast and Melief, 1991, and by Reinholdsson-Ljunggren et al., 1992).

We have succeeded in the identification of viral peptides that bind to the groove of MHC class I molecules by using the antigen processing defective cell line 174CEM.T2 generated and provided by P. Cresswell (see Salter and Cresswell, 1986). This cell line expresses the human MHC class I HLA-A2.1 and HLA-B5 alleles of which only the HLA-A2.1 molecules are expressed as partly empty and unstable molecules that can be stabilized on the cell surface with exogenously added peptides. If incubation with peptide results in an increase in the cell surface expression of this MHC molecule, this implies that the peptide binds to the groove of the HLA-A2.1 molecule and is therefore a possible candidate to be recognized by CTL. The HLA-A2.1 molecule is the most frequent HLA molecule present in the Western European Caucasoid population. About 50% of this population expresses this allele.

Using the amino acid sequence of the E6 and E7 proteins of HPV16 and HPV18 (Seedorf et al., 1985) we generated all possible nonapeptides (i.e. 9 amino acid long peptides) overspanning the entire E6 and E7 region. Every amino acid was used as a start amino acid for these 9-mer peptides. Every peptide was subjected individually to the above test to determine its capacity to bind to the HLA-A2.1 molecule. With respect to HPV16, we identified in total 10 peptides in the HPV16 E6 region and 8 in the HPV16 E7 region which bound to the HLA-A2.1 molecule in the above test. With respect to HPV18, in total 9 peptides in the HPV18 E6 region and 5 in the HPV18 E7 region were identified in the above test to bind to the HLA-A2.1 molecule. This implies that important candidate peptides of HPV16 and HPV18 for use as a vaccine in HLA-A2.1 positive humans have been identified.

By using a second approach, we succeeded to expand the list of HLA-A2.1 binding HPV peptides a little further and to determine HPV16 E6 and E7 peptides binding to other HLA molecules, viz. to the HLA-A1, HLA-A3.2, HLA-A11.2 and HLA-A24 molecules. Said second approach consisted of a competitive immunochemical peptide-MHC binding assay using purified class I molecules and radiolabeled consensus peptides.

SUMMARY OF THE INVENTION

An object of the present invention is to provide synthetic peptides which can be used for prevention, prophylaxis, therapy and treatment of cervical carcinoma and/or adenoma and other HPV-related, in particular HPV16- and/or HPV18-related diseases.

Another object of the invention is to provide a method of prophylactic or therapeutic treatment of cervical carcinoma and/or adenoma and other HPV-related, in particular HPV16- and/or HPV18-related diseases.

A further object of the present invention is to provide pharmaceutical compositions which can be used for prevention, prophylaxis, therapy and treatment of cervical carcinoma and/or adenoma and other HPV-related, in particular HPV16- and/or HPV18-related diseases.

This invention provides a peptide comprising an amino acid sequence derived from a protein of human papilloma virus (HPV), wherein said amino acid sequence has the ability to bind to a human Major Histocompatibility Complex (MHC) Class I molecule.

The present invention also provides specific peptides derived from the amino acid sequence of the E6 and E7 regions of HPV16 and HPV18 which, because of their capability to bind to HLA molecules, such as e.g. the HLA-A2.1, HLA-A1, HLA-A3.2, HLA-A11.2 or HLA-A24 protein, are candidate peptides to be included in human vaccines that can induce protective or therapeutic T cell responses against HPV16 and/or HPV18.

The novel peptides of the present invention are useful in pharmaceutical compositions, as screening tools and in the prevention, prophylaxis, therapy and treatment of HPV16- and/or HPV18-induced diseases or other conditions which would benefit from inhibition of HPV16 and/or HPV18 infection.

In a preferred embodiment of the invention, said amino acid sequence is derived from protein E6 or E7 of HPV16. In another preferred embodiment of the invention, said amino acid sequence is derived from protein E6 or E7 of HPV18.

Preferably, said amino acid sequence has the ability to bind to human MHC Class I allele HLA-A2.1.

More specifically, this invention provides a peptide comprising an amino acid sequence derived from protein E6 or E7 of HPV16, wherein said amino acid sequence has the ability to bind to human MHC Class I allele HLA-A2.1 and is selected from the group consisting of:
- AMFQDPQER (residues 7-15 of HPV16 protein E6) (SEQ ID NO:1)
- KLPQLCTEL (residues 18-26 of HPV16 protein E6) (SEQ ID NO:2)
- QLCTELQTT (residues 21-29 of HPV16 protein E6) (SEQ ID NO:3)
- LCTELQTTI (residues 22-30 of HPV16 protein E6) (SEQ ID NO:4)
- ELQTTIHDI (residues 25-33 of HPV16 protein E6) (SEQ ID NO:5)
- LQTTIHDII (residues 26-34 of HPV16 protein E6) (SEQ ID NO:6)
- TIHDIILEC (residues 29-37 of HPV16 protein E6) (SEQ ID NO:7)
- IHDIILECV (residues 30-38 of HPV16 protein E6) (SEQ ID NO:8)
- CVYCKQQLL (residues 37-45 of HPV16 protein E6) (SEQ ID NO:9)
- FAFRDLCIV (residues 52-60 of HPV16 protein E6) (SEQ ID NO:10)
- KISEYRHYC (residues 79-87 of HPV16 protein E6) (SEQ ID NO:11)
- PLCDLLIRC (residues 102-110 of HPV16 protein E6) (SEQ ID NO:12)
- TLHEYMLDL (residues 7-15 of HPV16 protein E7) (SEQ ID NO:13)
- YMLDLQPET (residues 11-19 of HPV16 protein E7) (SEQ ID NO:14)
- MLDLQPETT (residues 12-20 of HPV16 protein E7) (SEQ ID NO:15)
- RLCVQSTHV (residues 66-74 of HPV16 protein E7) (SEQ ID NO:16)
- TLEDLLMGT (residues 78-86 of HPV16 protein E7) (SEQ ID NO:17)
- LLMGTLGIV (residues 82-90 of HPV16 protein E7) (SEQ ID NO:18)
- GTLGIVCPI (residues 85-93 of HPV16 protein E7) (SEQ ID NO:19)
- TLGIVCPIC (residues 86-94 of HPV16 protein E7) (SEQ ID NO:20), and
- a fragment, homolog, isoform, derivative, genetic variant or conservative variant of any one of these amino acid sequences which has the ability to bind to human MHC Class I allele HLA-A2.1.

More specifically, this invention provides a peptide comprising an amino acid sequence derived from protein E6 or E7 of HPV18, wherein said amino acid sequence has the ability to bind to human MHC Class I allele HLA-A2.1 and is selected from the group consisting of:
- KLPDLCTEL (residues 13-21 of HPV18 protein E6) (SEQ ID NO:21)
- SLQDIEITC (residues 24-32 of HPV18 protein E6) (SEQ ID NO:22)
- LQDIEITCV (residues 25-33 of HPV18 protein E6) (SEQ ID NO:23)
- EITCVYCKT (residues 29-37 of HPV18 protein E6) (SEQ ID NO:24)
- KTVLELTEV (residues 36-44 of HPV18 protein E6) (SEQ ID NO:25)
- ELTEVFEFA (residues 40-48 of HPV18 protein E6) (SEQ ID NO:26)
- FAFKDLFVV (residues 47-55 of HPV18 protein E6) (SEQ ID NO:27)
- DTLEKLTNT (residues 88-96 of HPV18 protein E6) (SEQ ID NO:28)
- LTNTGLYNL (residues 93-101 of HPV18 protein E6) (SEQ ID NO:29)
- TLQDIVLHL (residues 7-15 of HPV18 protein E7) (SEQ ID NO:30)
- FQQLFLNTL (residues 86-94 of HPV18 protein E7) (SEQ ID NO:31)
- QLFLNTLSF (residues 88-96 of HPV18 protein E7) (SEQ ID NO:32)
- LFLNTLSFV (residues 89-97 of HPV18 protein E7) (SEQ ID NO:33)
- LSFVCPWCA (residues 94-102 of HPV18 protein E7) (SEQ ID NO:34), and
- a fragment, homolog, isoform, derivative, genetic variant or conservative variant of any one of these amino acid sequences which has the ability to bind to human MHC Class I allele HLA-A2.1.

According to another preferred embodiment of this invention, said amino acid sequence has the ability to bind to human MHC Class I allele HLA-A1.

More specifically, this invention provides a peptide comprising an amino acid sequence derived from protein E6 or E7 of HPV16, wherein said amino acid sequence has the ability to bind to human MHC Class I allele HLA-A1 and is selected from the group consisting of:
- YRDGNPYAV (residues 61-69 of HPV16 protein E6) (SEQ ID NO:35)
- WTGRCMSCC (residues 139-147 of HPV16 protein E6) (SEQ ID NO:36)
- MSCCRSSRT (residues 144-152 of HPV16 protein E6) (SEQ ID NO:37)
- TTDLYCYEQ (residues 19-27 of HPV16 protein E7) (SEQ ID NO:38)
- EIDGPAGQA (residues 37-45 of HPV16 protein E7) (SEQ ID NO:39)
- HVDIRTLED (residues 73-81 of HPV16 protein E7) (SEQ ID NO:40), and
- a fragment, homolog, isoform, derivative, genetic variant or conservative variant of any one of these amino acid sequences which has the ability to bind to human MHC Class I allele HLA-A1.

According to another preferred embodiment of this invention, said amino acid sequence has the ability to bind to human MHC Class I allele HLA-A3.2.

More specifically, this invention provides a peptide comprising an amino acid sequence derived from protein E6 or E7 of HPV16, wherein said amino acid sequence has the ability to bind to human MHC Class I allele HLA-A3.2 and is selected from the group consisting of:
- AMFQDPQER (residues 7-15 of HPV16 protein E6) (SEQ ID NO:1)
- IILECVYCK (residues 33-41 of HPV16 protein E6) (SEQ ID NO:41)
- CVYCKQQLL (residues 37-45 of HPV16 protein E6) (SEQ ID NO:9)
- VYCKQQLLR (residues 38-46 of HPV16 protein E6) (SEQ ID NO:42)

QQLLRREVY (residues 42-50 of HPV16 protein E6) (SEQ ID NO:43)
IVYRDGNPY (residues 59-67 of HPV16 protein E6) (SEQ ID NO:44)
YAVCDKCLK (residues 67-75 of HPV16 protein E6) (SEQ ID NO:45)
AVCDKCLKF (residues 68-76 of HPV16 protein E6) (SEQ ID NO:46)
VCDKCLKFY (residues 69-77 of HPV16 protein E6) (SEQ ID NO:47)
KFYSKISEY (residues 75-83 of HPV16 protein E6) (SEQ ID NO:48)
KISEYRHYC (residues 79-87 of HPV16 protein E6) (SEQ ID NO:11)
ISEYRHYCY (residues 80-88 of HPV16 protein E6) (SEQ ID NO:49)
RHYCYSLYG (residues 84-92 of HPV16 protein E6) (SEQ ID NO:50)
SLYGTTLEQ (residues 89-97 of HPV16 protein E6) (SEQ ID NO:51)
TTLEQQYNK (residues 93-101 of HPV16 protein E6) (SEQ ID NO:52)
QQYNKPLCD (residues 97-105 of HPV16 protein E6) (SEQ ID NO:53)
LIRCINCQK (residues 107-115 of HPV16 protein E6) (SEQ ID NO:54)
HLDKKQRFH (residues 125-133 of HPV16 protein E6) (SEQ ID NO:55)
CMSCCRSSR (residues 143-151 of HPV16 protein E6) (SEQ ID NO:56)
SCCRSSRTR (residues 145-153 of HPV16 protein E6) (SEQ ID NO:57)
CCRSSRTRR (residues 146-154 of HPV16 protein E6) (SEQ ID NO:58)
HYNIVTFCC (residues 51-59 of HPV16 protein E7) (SEQ ID NO:59)
YNIVTFCCK (residues 52-60 of HPV16 protein E7) (SEQ ID NO:60)
CCKCDSTLR (residues 58-66 of HPV16 protein E7) (SEQ ID NO:61)
KCDSTLRLC (residues 60-68 of HPV16 protein E7) (SEQ ID NO:62), and
a fragment, homolog, isoform, derivative, genetic variant or conservative variant of any one of these amino acid sequences which has the ability to bind to human MHC Class I allele HLA-A3.2.

According to another preferred embodiment of this invention, said amino acid sequence has the ability to bind to human MHC Class I allele HLA-A11.2.

More specifically, this invention-provides a peptide comprising an amino acid sequence derived from protein E6 or E7 of HPV16, wherein said amino acid sequence has the ability to bind to human MHC Class I allele HLA-A11.2 and is selected from the group consisting of:
AMFQDPQER (residues 7-15 of HPV16 protein E6) (SEQ ID NO:1)
IILECVYCK (residues 33-41 of HPV16 protein E6) (SEQ ID NO:41)
CVYCKQQLL (residues 37-45 of HPV16 protein E6) (SEQ ID NO:9)
VYCKQQLLR (residues 38-46 of HPV16 protein E6) (SEQ ID NO:42)
QQLLRREVY (residues 42-50 of HPV16 protein E6) (SEQ ID NO:43)
IVYRDGNPY (residues 59-67 of HPV16 protein E6) (SEQ ID NO:44)
YAVCDKCLK (residues 67-75 of HPV16 protein E6) (SEQ ID NO:45)
AVCDKCLKF (residues 68-76 of HPV16 protein E6) (SEQ ID NO:46)
VCDKCLKFY (residues 69-77 of HPV16 protein E6) (SEQ ID NO:47)
KISEYRHYC (residues 79-87 of HPV16 protein E6) (SEQ ID NO:11)
ISEYRHYCY (residues 80-88 of HPV16 protein E6) (SEQ ID NO:49)
LIRCINCQK (residues 107-115 of HPV16 protein E6) (SEQ ID NO:54)
TGRCMSCCR (residues 140-148 of HPV16 protein E6) (SEQ ID NO:63)
CMSCCRSSR (residues 143-151 of HPV16 protein E6) (SEQ ID NO:56)
SCCRSSRTR (residues 145-153 of HPV16 protein E6) (SEQ ID NO:57)
HYNIVTFCC (residues 51-59 of HPV16 protein E7) (SEQ ID NO:59)
YNIVTFCCK (residues 52-60 of HPV16 protein E7) (SEQ ID NO:60)
CCKCDSTLR (residues 58-66 of HPV16 protein E7) (SEQ ID NO:61)
VCPICSQKP (residues 90-98 of HPV16 protein E7) (SEQ ID NO:61), and
a fragment, homolog, isoform, derivative, genetic variant or conservative variant of any one of these amino acid sequences which has the ability to bind to human MHC Class I allele HLA-A11.2.

According to another preferred embodiment of this invention, said amino acid sequence has the ability to bind to human MHC Class I allele HLA-A24.

More specifically, this invention provides a peptide comprising an amino acid sequence derived from protein E6 or E7 of HPV16, wherein said amino acid sequence has the ability to bind to human MHC Class I allele HLA-A24 and is selected from the group consisting of:
MHQKRTAMF (residues 1-9 of HPV16 protein E6) (SEQ ID NO:65)
LQTTIHDII (residues 26-34 of HPV16 protein E6) (SEQ ID NO:6)
VYCKQQLLR (residues 38-46 of HPV16 protein E6) (SEQ ID NO:42)
LLRREVYDF (residues 44-52 of HPV16 protein E6) (SEQ ID NO:66)
VYDFAFRDL (residues 49-57 of HPV16 protein E6) (SEQ ID NO:67)
PYAVCDKCL (residues 66-74 of HPV16 protein E6) (SEQ ID NO:68)
KCLKFYSKI (residues 72-80 of HPV16 protein E6) (SEQ ID NO:69)
EYRHYCYSL (residues 82-90 of HPV16 protein E6) (SEQ ID NO:70)
HYCYSLYGT (residues 85-93 of HPV16 protein E6) (SEQ ID NO:71)
CYSLYGTTL (residues 87-95 of HPV16 protein E6) (SEQ ID NO:72)
RFHNIRGRW (residues 131-139 of HPV16 protein E6) (SEQ ID NO:73)
RAHYNIVTF (residues 49-57 of HPV16 protein E7) (SEQ ID NO:74), and
a fragment, homolog, isoform, derivative, genetic variant or conservative variant of any one of these amino acid sequences which has the ability to bind to human MHC Class I allele HLA-A24.

This invention further provides a pharmaceutical composition containing a prophylactically or therapeutically effective amount of a peptide according to the invention, and a pharmaceutically acceptable carrier, diluent, excipient or adjuvant. Preferably, said pharmaceutical composition contains a peptide according to the invention which is able to induce a T cell response effective against HPV, in particular a HLA class I-restricted CD8⁺ cytotoxic T cell response.

In addition, this invention provides a method of prophylactic or therapeutic treatment of cervical carcinoma and other HPV-related diseases with a human individual, comprising administering to said human individual a prophylactically or therapeutically effective amount of a peptide according to the invention, more specifically an immunogenic form of a peptide according to the invention which is able to induce a T cell response effective against HPV, in particular a HLA class I-restricted CD8⁺ cytotoxic T cell response.

DETAILED DESCRIPTION OF THE INVENTION

Figure 1:
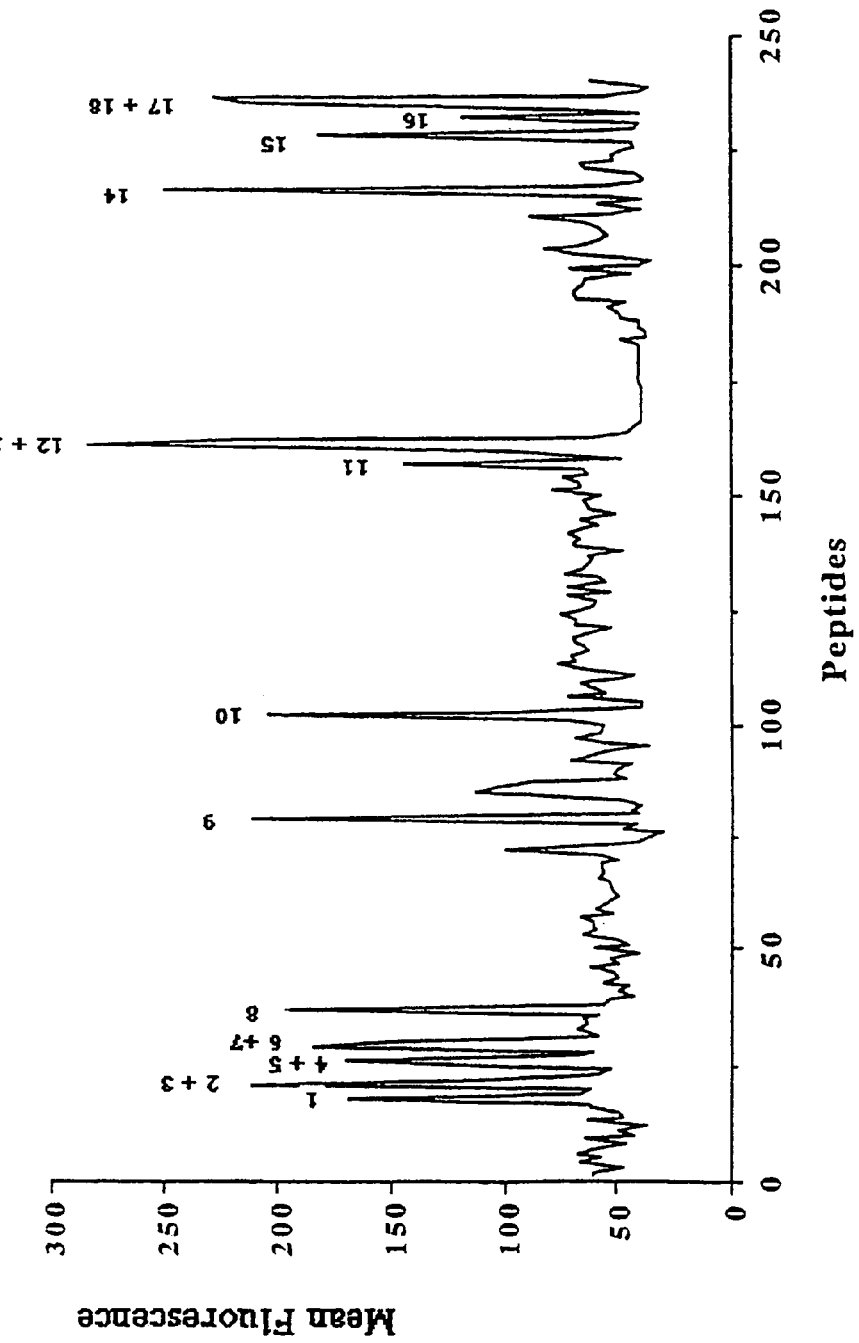
FIG. 1 gives the result of binding analyses of 240 HPV16 E6 and E7 nonapeptides to HLA-A2.1 expressed on 174CEM.T2 cells. Background fluorescence level (without adding peptides) was set on an arbitrary mean fluorescence level of 70. Binding of a peptide was regarded positive when twice the level of background fluorescence was reached. The 18 binding peptides are numbered 1 to 18; this numbering corresponds to the numbering in Table I.

The invention is directed to peptides comprising an amino acid sequence derived from a protein of HPV, wherein said amino acid sequence has the ability to bind to a human MHC Class I molecule. In view of our own experience with other viruses, the best candidates for induction of HLA class I restricted CD8⁺ cytotoxic T cells are the strongest binding peptides.

A most preferred embodiment of the invention concerns peptides comprising an amino acid sequence derived from protein E6 or E7 of HPV16, wherein said amino acid sequence has the ability to bind to human MHC Class I allele HLA-A2.1. Specifically, such peptides comprise the following amino acid sequences derived from the noted regions of HPV16 (see Table I; the amino acids are identified by the one-letter code of amino acids).

TABLE I

Peptides derived from HPV16 proteins E6 and E7 binding to HLA-A2.1

| Peptide No. | Amino acid sequence | protein (region) | SEQ ID NO |
|---|---|---|---|
| — | AMFQDPQER | E6 (residues 7-15) | 1 |
| 1 | KLPQLCTEL | E6 (residues 18-26) | 2 |
| 2 | QLCTELQTT | E6 (residues 21-29) | 3 |
| 3 | LCTELQTTI | E6 (residues 22-30) | 4 |
| 4 | ELQTTIHDI | E6 (residues 25-33) | 5 |
| 5 | LQTTIHDII | E6 (residues 26-34) | 6 |
| 6 | TIHDIILEC | E6 (residues 29-37) | 7 |
| 7 | IHDIILECV | E6 (residues 30-38) | 8 |
| 8 | CVYCKQQLL | E6 (residues 37-45) | 9 |
| — | FAFRDLCIV | E6 (residues 52-60) | 10 |
| 9 | KISEYRHYC | E6 (residues 79-87) | 11 |
| 10 | PLCDLLIRC | E6 (residues 102-110) | 12 |
| 11 | TLHEYMLDL | E7 (residues 7-15) | 13 |
| 12 | YMLDLQPET | E7 (residues 11-19) | 14 |
| 13 | MLDLQPETT | E7 (residues 12-20) | 15 |
| 14 | RLCVQSTHV | E7 (residues 66-74) | 16 |
| 15 | TLEDLLMGT | E7 (residues 78-86) | 17 |
| 16 | LLMGTLGIV | E7 (residues 82-90) | 18 |
| 17 | GTLGIVCPI | E7 (residues 85-93) | 19 |
| 18 | TLGIVCPIC | E7 (residues 86-94) | 20 |

Another most preferred embodiment of the invention concerns peptides comprising an amino acid sequence derived from protein E6 or E7 of HPV18, wherein said amino acid sequence has the ability to bind to human MHC Class I allele HLA-A2.1. Specifically, such peptides comprise the following amino acid sequences derived from the noted regions of HPV18 (see Table II; the amino acids are identified by the one-letter code of amino acids).

TABLE II

Peptides derived from HPV18 proteins E6 and E7 binding to HLA-A2.1

| Peptide No. | Amino acid sequence | protein (region) | SEQ ID NO |
|---|---|---|---|
| 1 | KLPDLCTEL | E6 (residues 13-21) | 21 |
| 2 | SLQDIEITC | E6 (residues 24-32) | 22 |
| 3 | LQDIEITCV | E6 (residues 25-33) | 23 |
| 4 | EITCVYCKT | E6 (residues 29-37) | 24 |
| 5 | KTVLELTEV | E6 (residues 36-44) | 25 |
| 6 | ELTEVFEFA | E6 (residues 40-48) | 26 |
| 7 | FAFKDLFVV | E6 (residues 47-55) | 27 |
| 8 | DTLEKLTNT | E6 (residues 88-96) | 28 |
| 9 | LTNTGLYNL | E6 (residues 93-101) | 29 |
| 10 | TLQDIVLHL | E7 (residues 7-15) | 30 |
| 11 | FQQLFLNTL | E7 (residues 86-94) | 31 |
| 12 | QLFLNTLSF | E7 (residues 88-96) | 32 |
| 13 | LFLNTLSFV | E7 (residues 89-97) | 33 |
| 14 | LSFVCPWCA | E7 (residues 94-102) | 34 |

Another preferred embodiment of the invention concerns peptides comprising an amino acid sequence derived from protein E6 or E7 of HPV16, wherein said amino acid sequence has the ability to bind to human MHC Class I allele HLA-A1. Specifically, such peptides comprise the following amino acid sequences derived from the noted regions of HPV16 (see Table III; the amino acids are identified by the one-letter code of amino acids).

TABLE III

Peptides derived from HPV16 proteins E6 and E7 binding to HLA-A1

| Amino acid sequence | protein (region) | SEQ ID NO |
|---|---|---|
| YRDGNPYAV | E6 (residues 61-69) | 35 |
| WTGRCMSCC | E6 (residues 139-147) | 36 |
| MSCCRSSRT | E6 (residues 144-152) | 37 |
| TTDLYCYEQ | E7 (residues 19-27) | 38 |
| EIDGPAGQA | E7 (residues 37-45) | 39 |
| HVDIRTLED | E7 (residues 73-81) | 40 |

Another preferred embodiment of the invention concerns peptides comprising an amino acid sequence derived from protein E6 or E7 of HPV16, wherein said amino acid sequence has the ability to bind to human MHC Class I allele HLA-A3.2. Specifically, such peptides comprise the following amino acid sequences derived from the noted regions of HPV16 (see Table IV; the amino acids are identified by the one-letter code of amino acids).

TABLE IV

Peptides derived from HPV16 proteins E6 and E7 binding to HLA-A3.2

| Amino acid sequence | protein (region) | SEQ ID NO |
|---|---|---|
| AMFQDPQER | E6 (residues 7-15) | 1 |
| IILECVYCK | E6 (residues 33-41) | 41 |
| CVYCKQQLL | E6 (residues 37-45) | 9 |
| VYCKQQLLR | E6 (residues 38-46) | 42 |
| QQLLRREVY | E6 (residues 42-50) | 43 |
| IVYRDGNPY | E6 (residues 59-67) | 44 |
| YAVCDKCLK | E6 (residues 67-75) | 45 |
| AVCDKCLKF | E6 (residues 68-76) | 46 |
| VCDKCLKFY | E6 (residues 69-77) | 47 |
| KFYSKISEY | E6 (residues 75-83) | 48 |
| KISEYRHYC | E6 (residues 79-87) | 11 |
| ISEYRHYCY | E6 (residues 80-88) | 49 |
| RHYCYSLYG | E6 (residues 84-92) | 50 |
| SLYGTTLEQ | E6 (residues 89-97) | 51 |
| TTLEQQYNK | E6 (residues 93-101) | 52 |
| QQYNKPLCD | E6 (residues 97-105) | 53 |
| LIRCINCQK | E6 (residues 107-115) | 54 |
| HLDKKQRFH | E6 (residues 125-133) | 55 |
| CMSCCRSSR | E6 (residues 143-151) | 56 |
| SCCRSSRTR | E6 (residues 145-153) | 57 |
| CCRSSRTRR | E6 (residues 146-154) | 58 |
| HYNIVTFCC | E7 (residues 51-59) | 59 |
| YNIVTFCCK | E7 (residues 52-60) | 60 |
| CCKCDSTLR | E7 (residues 58-66) | 61 |
| KCDSTLRLC | E7 (residues 60-68) | 62 |

Another preferred embodiment of the invention concerns peptides comprising an amino acid sequence derived from protein E6 or E7 of HPV16, wherein said amino acid sequence has the ability to bind to human MHC Class I allele HLA-A11.2. Specifically, such peptides comprise the following amino acid sequences derived from the noted regions of HPV16 (see Table V; the amino acids are identified by the one-letter code of amino acids).

TABLE V

Peptides derived from HPV16 proteins E6 and E7 binding to HLA-A11.2

| Amino acid sequence | protein (region) | SEQ ID NO |
|---|---|---|
| AMFQDPQER | E6 (residues 7-15) | 1 |
| IILECVYCK | E6 (residues 33-41) | 41 |

TABLE V-continued

Peptides derived from HPV16 proteins E6 and E7 binding to HLA-A11.2

| Amino acid sequence | protein (region) | SEQ ID NO |
|---|---|---|
| CVYCKQQLL | E6 (residues 37-45) | 9 |
| VYCKQQLLR | E6 (residues 38-46) | 42 |
| QQLLRREVY | E6 (residues 42-50) | 43 |
| IVYRDGNPY | E6 (residues 59-67) | 44 |
| YAVCDKCLK | E6 (residues 67-75) | 45 |
| AVCDKCLKF | E6 (residues 68-76) | 46 |
| VCDKCLKFY | E6 (residues 69-77) | 47 |
| KISEYRHYC | E6 (residues 79-87) | 11 |
| ISEYRHYCY | E6 (residues 80-88) | 49 |
| LIRCINCQK | E6 (residues 107-115) | 54 |
| TGRCMSCCR | E6 (residues 140-148) | 63 |
| CMSCCRSSR | E6 (residues 143-151) | 56 |
| SCCRSSRTR | E6 (residues 145-153) | 57 |
| HYNIVTFCC | E7 (residues 51-59) | 59 |
| YNIVTFCCK | E7 (residues 52-60) | 60 |
| CCKCDSTLR | E7 (residues 58-66) | 61 |
| VCPICSQKP | E7 (residues 90-98) | 64 |

Another preferred embodiment of the invention concerns peptides comprising an amino acid sequence derived from protein E6 or E7 of HPV16, wherein said amino acid sequence has the ability to bind to human MHC Class I allele HLA-A24. Specifically, such peptides comprise the following amino acid sequences derived from the noted regions of HPV16 (see Table VI; the amino acids are identified by the one-letter code of amino acids).

TABLE VI

Peptides derived from HPV16 proteins E6 and E7 binding to HLA-A24

| Amino acid sequence | protein (region) | SEQ ID NO |
|---|---|---|
| MHQKRTAMF | E6 (residues 1-9) | 65 |
| LQTTIHDII | E6 (residues 26-34) | 6 |
| VYCKQQLLR | E6 (residues 38-46) | 42 |
| LLRREVYDF | E6 (residues 44-52) | 66 |
| VYDFAFRDL | E6 (residues 49-57) | 67 |
| PYAVCDKCL | E6 (residues 66-74) | 68 |
| KCLKFYSKI | E6 (residues 72-80) | 69 |
| EYRHYCYSL | E6 (residues 82-90) | 70 |
| HYCYSLYGT | E6 (residues 85-93) | 71 |
| CYSLYGTTL | E6 (residues 87-95) | 72 |
| RFHNIRGRW | E6 (residues 131-139) | 73 |
| RAHYNIVTF | E7 (residues 49-57) | 74 |

The data suggest that the peptides mentioned above are single polypeptides of identified sequences. However, homologs, isoforms or genetic variants of these peptides may exist within or outside the cellular environment. This invention encompasses all such homologs, isoforms or genetic variants of the above peptides provided that they bind to the HLA molecule in question.

Polypeptides that are homologs of the peptides specifically include those having amino acid sequences which are at least about 40% conserved in relation to the amino acid sequence set forth in Tables I-VI, preferentially at least about 60% conserved, and more referentially at least about 75% conserved.

It will be understood by one of ordinary skill in the art that other variants of the peptides shown above are included within the scope of the present invention. This particularly includes any variants that differ from the above mentioned and synthesized peptides only by conservative amino acid substitution. In particular, replacements of C (cysteine) by A (alanine), S (serine), α-aminobutyric acid and others are included as it is known that cysteine-containing peptides are susceptible to (air) oxidation during synthesis and handling. Many such conservative amino acid substitutions are set forth as sets by Taylor (1986).

Herein the peptides shown above or fragments thereof include any variation in the amino acid sequence, whether by conservative amino acid substitution, deletion, or other processes, provided that the polypeptides bind to the HLA molecule in question. The fragments of the peptides may be small peptides with sequences of as little as five or more amino acids, said sequences being those disclosed in Tables I-VI when said polypeptides bind to the HLA molecule in question.

Polypeptides larger than the peptides shown are especially included within the scope of the present invention when said polypeptides induce a HPV16- or HPV18-specific CTL response in appropriate individuals (e.g. HLA-A2.1 positive individuals in the case of HLA-A2.1 binding peptides) and include a (partial) amino acid sequence as set forth in Tables I-VI, or conservative substitutions thereof. Such polypeptides may have a length up to about 30 amino acids, preferably up to about 27 amino acids. Most preferably, however, the peptides have a length of from 9 to 12, more preferably 9 to 11 or even 9 to 10 amino acids, most of all preferably exactly 9 amino acids.

This invention includes the use of polypeptides generated by every means, whether genetic engineering, peptide synthesis with solid phase techniques or others. The foregoing peptides may have various chemical modifications made at the terminal ends and still be within the scope the present invention. Also other chemical modifications are possible, particularly cyclic and dimeric configurations. The term "derivatives" intends to cover all such modified peptides.

The polypeptides of the present invention find utility for the treatment or prevention of diseases involving HPV16 or HPV18 such as genital warts, cervical cancer or others that are linked to HPV16 or HPV18.

For all applications the peptides are administered in an immunogenic form. Since the peptides are relatively short, this may necessitate conjugation with an immunogenicity conferring carrier material such as lipids or others or the use of adjuvants.

The magnitude of a prophylactic or a therapeutic dose of polypeptides of this invention will, of course, vary with the group of patients (age, sex, weight, etcetera), the nature of the severity of the condition to be treated, the particular polypeptide of this invention and its route of administration. Any suitable route of administration may be employed to achieve an effective dosage of a polypeptide identified by this invention, as well as any dosage form well known in the art of pharmacy. In addition the polypeptides may also be administered by controlled release means and/or delivery devices. They may also be administered in combination with other active substances, such as, in particular, T-cell activating agents like interleukine-2 etc.

The peptides of this invention may also be useful for other purposes, such as diagnostic use. For example, they may be used to check whether a vaccination with a peptide according to the invention has been successful. This may be done in vitro by testing whether said peptide is able to activate T cells of the vaccinated person.

The following examples illustrate the present invention without limiting the same thereto.

EXAMPLE 1

Materials
Peptide Synthesizer:
Abimed AMS 422 (Abimed Analysen-Technik GmbH, Langenfeld, Germany).
Synthesis Polymer:
Tentagel S AC (0.17-0.24 meq/g, Rapp Polymere, Tübingen, Germany).
HPLC Equipment:
The HPLC system used for analysis and purification of peptides consisted of: autosampler 2157, HPLC pump 2248, variable wavelength monitor VWM 2141, column oven 2155, low pressure mixer, all of Pharmacia Nederland B.V., Woerden, The Netherlands, a Star LC-20 dot matrix printer, Star Micronics Co., Ltd., all parts controlled by a Tandon PCAs1/386sx computer, Tandon Computer Benelux B.V., Amsterdam, The Netherlands.
Lyophylizer:
Virtis Centry, The Virtis Company, Inc., Gardiner (N.Y.), USA, equipped with an Alcatel 350C vacuumpump, Alcatel CIT, Malakoff, France, connected to a Christ Alpha RVC vacuo-spin, Martin Christ Gefriertrocknungsanlagen GmbH, Osterode am Harz, Germany.
Centrifuge:
MSE Mistral 6L, Beun de Ronde, Abcoude, The Netherlands.
Mass Spectrometer:
Bioion plasma desorption mass spectrometer (PDMS), Applied Biosystems, Inc., Foster City (Calif.), USA.
Amino Acid Analysis:
HP Aminoquant, Hewlett Packard, Amstelveen, The Netherlands.
Chemicals:
All chemicals were used without further purification unless stated otherwise.
Fmoc (9-fluorenylmethyloxycarbonyl) amino acids were of the L-configuration, bearing the following side chain protecting groups: t-Bu (tert-butyl) for Asp, Glu, Tyr, Ser and Thr; Trt (trityl) for His, Asn and Gln; Pmc (2,2,5,7,8-pentamethylchroman-6-sulfonyl) for Arg; Boc (tert-butyloxycarbonyl) for Lys, all Novasyn and purchased from Pharmacia Nederland B.V., Woerden, The Netherlands.
Piperidine was purchased from Aldrich Chemie Benelux N.V., Brussels, Belgium.
BOP (benzotriazole-1-yl-oxy-tris-(dimethylamino)-phosphonium hexafluorophosphate) was obtained from Richelieu Biotechnologies, St-Hyacinthe, Canada.
N-methylmorpholin (NMM, Janssen Chimica, Tilburg, The Netherlands) was distilled from NaOH at atmospheric pressure before use.
N-methylpyrrolidone (NMP, Aldrich Chemie) was vacuum-distilled under a nitrogen atmosphere (b.p. 78-80° C., 18 mm Hg) before use.
Acetonitrile (HPLC-grade) was purchased from Rathburn Chemicals Ltd., Walkerburn, Scotland.
Ether (Baker Analyzed grade), pentane (Baker grade) and acetic acid (Baker Analyzed grade) were purchased from J. T. Baker B.V., Deventer, The Netherlands.
Ethanethiol was obtained from Fluka Chemie, Brussels, Belgium.
Dichloromethane and N,N-dimethylacetamide (DMA) were purchased from Janssen Chimica, Tilburg, The Netherlands.
Trifluoroacetic acid (TFA, z.S. grade) was obtained from Merck-Schuchardt, Hohenbrunn, Germany.

Disposables:

Polypropylene reaction vessels containing a PTFE filter were purchased from Abimed Analysen-Technik GmbH, Langenfeld, Germany.

All other disposables used were made of polypropylene and obtained from Sarstedt B.V., Etten-Leur, The Netherlands.

Experimental Conditions:

All experiments were performed at room temperature unless stated otherwise. All Fmoc protected aminoacids, synthesis polymers, peptides and TFA were stored at −20° C.

Peptide Synthesis

Peptides were synthesized by solid phase strategies on an automated multiple peptide synthesizer (Abimed AMS 422) (see Gausepohl and Frank, 1990; Gausepohl et al., 1990).

The peptides were made in various runs, in each of which 48 different peptides were synthesized simultaneously.

Tentagel S AC (Rapp et al., 1990; Sheppard and Williams, 1982), a graft polymer of polyethyleneglycol spacer arms on a polystyrene matrix, was used as a resin (40-60 mg per peptide, 10 µmol Fmoc amino acid loading).

Repetitive couplings were performed by adding a mixture of 90 µl 0.67 M BOP (Gausepohl et al., 1988; Castro et al., 1975) in NMP, 20 µl NMM in NMP 2/1 (v/v) and 100 µl of an 0.60 M solution of the appropriate Fmoc amino acid (Fields and Noble, 1990) in NMP (6-fold excess) to each reaction vessel. At 70% of the reaction time approximately 50 µl dichloromethane was added to each reaction vessel.

Fmoc-deprotection was performed by adding 3 times 0.8 ml of piperidine/DMA 1/4 (v/v) to each reaction vessel.

Coupling- and deprotection times were increased as the synthesis proceeded, starting with 30 min and 3 times 3 min respectively.

Washings after couplings and Fmoc-deprotections were done with 6 times 1.2 ml DMA. After the required sequence had been reached and the last Fmoc-protection was removed the peptidylresin was washed extensively with DMA, dichloromethane, dichloromethane/ether 1/1 (v/v) and ether respectively, and dried.

Peptide Cleavage and Isolation

Cleavage of the peptides from the resin and removal of the side chain protecting groups was performed by adding 6 times 200 µl TFA/water 19/1 (v/v) at 5 min intervals to each reaction vessel, thus yielding free carboxylic peptides. For Trp-containing peptides TFA/water/ethanethiol 18/1/1 (v/v/v) was used.

Two hours after the first TFA addition the peptides were precipitated from the combined filtrates by addition of 10 ml ether/pentane 1/1 (v/v) and cooling to −20° C. The peptides were isolated by centrifugation (−20° C., 2500 g, 10 min).

After treatment of the pellet with ether/pentane 1/1 (v/v) and isolation by the same centrifugation procedure, the peptides were dried at 45° C. for 15 min.

Each of the peptides was dissolved in 2 ml water (or 2 ml 10 vol. % acetic acid), the solution frozen in liquid nitrogen for 3 min, and lyophylized while being centrifuged (1300 rpm, 8-16 h).

Analysis and Purification

The purity of the peptides was determined by reversed phase HPLC; an aliquot of about 50 nmol was dissolved in 100 µl 30 vol. % acetic acid. Of this solution 30 µl was applied to an RP-HPLC system equipped with a ternary solvent system; A: water, B: acetonitrile, C: 2 vol. % TFA in water.

Gradient elution (1.0 ml/min) was performed from 90% A, 5% B, 5% C to 20% A, 75% B, 5% C in 30 min. Detection was at 214 nm.

Samples taken at random were analysed by mass spectrometry on a PDMS. The 31 binding peptides were all analysed by mass spectrometry on a PDMS and by quantative amino acid analysis after hydrolysis on a HP Aminoquant. Of all analysed samples the difference between calculated and measured masses was within the experimental error (0.1%) as specified by the producer of the equipment used. All aminoacid compositions were as expected.

EXAMPLE 2

Peptides

Of all 240 HPV16 peptides and 247 HPV18 peptides that had been freeze dried, 5 mg was weighed and dissolved in 1 ml of distilled water adjusted with 5N NaOH to a pH of 12. Peptides that did not readily dissolve were treated with 150 µl of 100% acetic acid glacial ($CH_3COOH$, Merck Darmstadt, Germany: 56-1000) after which the pH was neutralized to pH7 with 5N NaOH diluted in distilled water (Merck Darmstadt, Germany: 6498). Peptides which still did not dissolve were treated with 100 µl of 5N NaOH to pH 12 after which the pH was neutralized to pH 7 with 10% acetic acid glacial in distilled water. Of all peptides a dilution of 1 mg/ml in 0.9% NaCl was made.

Cells

174CEM.T2 cells were cultured in Iscovel's modified Dulbecco's medium (Biochrom KG Seromed Berlin, Germany: F0465) supplemented with 100 IU/ml penicillin (Biocades Pharma, Leiderdorp, The Netherlands), 100 µg/ml kanamycin (Sigma St. Louis, USA:K-0254), 2 mM glutamine (ICN Biomedicals Inc. Costa Mesa, Calif., USA: 15-801-55) and 10% fetal calf serum (FCS, Hyclone Laboratories Inc. Logan, Utah, USA:A-1115-L). Cells were cultured at a density of $2.5 \times 10^5$/ml during 3 days at 37° C., 5% $CO_2$ in humified air.

Peptide Binding

174CEM.T2 cells were washed twice in culture medium without FCS and put in serum-free culture medium to a density of $2 \times 10^6$ cells/ml. Of this suspension 40 µl was put into a V bottomed 96 well plate (Greiner GmbH, Frickenhausen, Germany: 651101) together with 10 µl of the individual peptide dilutions (of 1 mg/ml). The end concentration is 200 µg/ml peptide with $8 \times 10^4$ 174CEM.T2 cells. This solution was gently agitated for 3 minutes after which an incubation time of 16 hours at 37° C., 5% $CO_2$ in humified air took place. Then cells were washed once with 100 µl 0.9% NaCl, 0.5% bovine serum albumin (Sigma St. Louis, USA: A-7409), 0.02% $NaN_3$ (Merck Darmstadt, Germany: 822335). After a centrifuge round of 1200 rpm the pellet was resuspended in 50 µl of saturating amounts of HLA-A2.1 specific mouse monoclonal antibody BB7.2 for 30 minutes at 4° C. Then cells were washed twice and incubated for 30 minutes with $F(ab)_2$ fragments of goat anti-mouse IgG that had been conjugated with fluorescence isothiocyanate (Tago Inc Burlingame, Calif., USA: 4350) in a dilution of 1:40 and a total volume of 25 µl.

Figure 2:
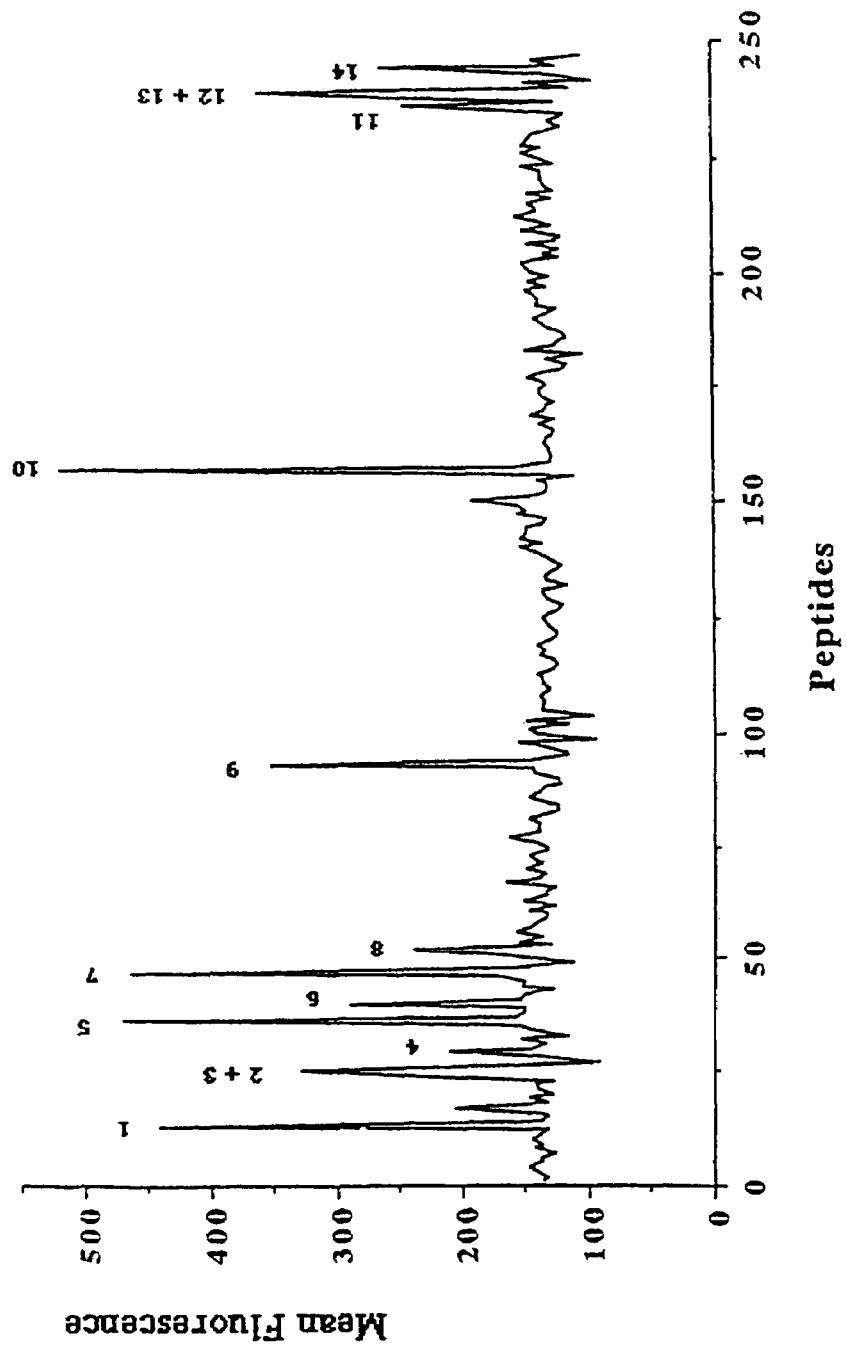
FIG. 2 gives the result of binding analyses of 247 HPV18 E6 and E7 nonapeptides to HLA-A2.1 expressed on 174CEM.T2 cells. Background fluorescence level (without adding peptides) was set on an arbitrary mean fluorescence level of 70. Binding of a peptide was regarded positive when twice the level of background fluorescence was reached. The 14 binding peptides are numbered 1 to 14; this numbering corresponds to the numbering in Table II.

After the last incubation, cells were washed twice and fluorescence was measured at 488 nanometer on a FACScan flow-cytometer (Becton Dickinson, Franklin Lakes, N.J., USA). The results are shown in FIG. 1 (HPV16 peptides) and FIG. 2 (HPV18 peptides), respectively.

The 174CEM.T2 cell line expresses "empty" and unstable HLA-A2.1 molecules that can be stabilized when a peptide is binding to the peptide presenting groove of these molecules. A stabilized HLA-A2.1 molecule that will not easily degrade is the result of binding of an analyzed peptide. This leads to an increase in cell surface expression of the HLA-A2.1 molecule.

Results

In order to identify E6 and E7 region peptides of HPV16 and HPV18 that could bind to HLA-A2.1 molecules expressed by 174CEM.T2 cells, the amino acid sequences of E6 and E7 of HPV16 and HPV18 were examined (4). Every amino acid in the E6 and E7 region was used as the first amino acid of a 9 amino acid long peptide. In this way the entire E6 and E7 regions of HPV16 and HPV18 were covered. Nine amino acid long peptides were chosen because they fit the presently known rules for length of peptides that bind to the groove of HLA-A2.1 molecules (reviewed by Kast and Melief, 1991). For practical reasons, in a first series of experiments alanine residues were used in the tested peptides instead of the cysteine residues occurring in the natural sequence. Thereafter, a second series of experiments was carried out with peptides containing the cysteine residues of the natural sequence.

Only the peptides Nos. 1-18 of Table I and Nos. 1-14 of Table II (including those containing alanine residues instead of the cysteine residues) were able to significantly upregulate the expression of HLA-A2.1 molecules measured as mean HLA-A2.1 fluorescence of 174CEM.T2 cells indicating their binding to the HLA-A2.1 molecule as described in Example 2. None of the 222+233 other peptides were able to do this. The results of the fluorescence measurement are given in Tables VII and VIII and shown in FIGS. 1 and 2. The peptides are numbered in accordance with the numbering in Tables I and II.

$$MF = \text{Mean Fluorescence}$$

$$FI = \text{Fluorescence Index} = \frac{(MF)_{experiment} - (MF)_{blank}}{(MF)_{blank}}$$

With background fluorescence level (without adding peptides) set on a Fluorescence Index level of 0, binding of a peptide was regarded positive when the level of fluorescence was ≥0.5.

TABLE VII

HPV16 peptides

| Peptide | FI | MF |
|---|---|---|
| 1 | 1.6 | 168.6 |
| 2 | 2.2 | 211.9 |
| 3 | 0.7 | 113.6 |
| 4 | 0.6 | 108.0 |
| 5 | 1.6 | 170.4 |
| 6 | 1.8 | 184.5 |
| 7 | 1.3 | 150.7 |
| 8 | 2.0 | 195.0 |
| 9 | 2.2 | 211.7 |
| 10 | 2.1 | 204.8 |
| 11 | 1.2 | 144.5 |
| 12 | 3.3 | 283.9 |
| 13 | 2.3 | 217.6 |
| 14 | 2.8 | 250.0 |
| 15 | 1.8 | 182.8 |
| 16 | 0.8 | 118.8 |

TABLE VII-continued

HPV16 peptides

| Peptide | FI | MF |
|---|---|---|
| 17 | 2.3 | 216.1 |
| 18 | 2.5 | 227.8 |

TABLE VIII

HPV18 peptides

| Peptide | FI | MF |
|---|---|---|
| 1 | 2.1 | 439.3 |
| 2 | 0.7 | 243.9 |
| 3 | 1.3 | 327.8 |
| 4 | 0.5 | 206.0 |
| 5 | 2.3 | 467.5 |
| 6 | 1.1 | 289.0 |
| 7 | 2.3 | 462.9 |
| 8 | 0.7 | 238.2 |
| 9 | 1.5 | 352.5 |
| 10 | 2.7 | 519.6 |
| 11 | 0.8 | 244.5 |
| 12 | 0.8 | 258.2 |
| 13 | 1.6 | 360.3 |
| 14 | 0.9 | 262.0 |

These experiments indicate that only a limited proportion of peptides have the ability to bind to the HLA-A2.1 molecule and are therefore the only candidates of the HPV16 and HPV18 E regions to be recognized by human CTL because CTL recognize peptides only when bound to HLA molecules.

EXAMPLE 3

This example illustrates in vitro induction of primary immune response against HPV peptides using the processing defective cell line 174CEM.T2.

The expression of HLA-A2.1 on 174CEM.T2 cells (T2) is increased by incubating T2 cells in medium containing relevant peptide. T2 cells will present the relevant peptide bound to HLA-A2.1 in high amount and therefore are good antigen presenting cells (APC). In the response inducing method described below the T2 cell line is used as APC and post-Ficoll mononuclear cells are used as responder cells.

Method

1) Peptide Loading of HLA-A2.1 on T2

T2 cells in a concentration of $2 \times 10^6$ cells per ml were incubated for 13 h at 37° C. in a T 25 flask (Becton Dickinson, Falcon, Plymouth Engeland cat.nr. 3013) in serum-free IMDM (=Iscoves Modified Dulbecco's Medium: Biochrom KG, Seromed Berlin, Germany, cat.nr. F0465) with glutamine (2 mM, ICN Biochemicals Inc., Costa Meisa, USA, cat.nr. 15-801-55), antibiotics (100 IU/ml penicilline (Brocades Pharma, Leiderdorp, The Netherlands, 100 μg/ml kanamycine (Sigma, St. Louis, USA, K-0245)) and the selected peptide MLDLQPETT (=JWK3; SEQ ID NO:15) in a concentration of 80 μg/ml.

2) Mitorycine C Treatment of T2 (APC)

These incubated T2 cells were spun down and subsequently treated in a density of $20 \times 10^6$ cells/ml with Mitomycine C (50 μg/ml) in serum-free RPMI (Gibco Paislan, Scotland, cat.nr. 041-02409) medium for 1 h at 37° C. Hereafter the T2 cells were washed three times in RPMI.

3) Preparing for Primary Immune Response Induction

All wells of a 96-well-U-bottom plate (Costar, Cambridge, USA, cat.nr. 3799) were filled with 100,000 Mitomycine C-treated T2 cells in 50 µl serum-free, complete RPMI medium (glutamine (2 mM, ICN Biochemicals Inc., Costa Meisa, USA, cat.nr. 15-801-55), penicilline (100 IU/ml, Brocades Pharma, Leiderdorp, The Netherlands), kanamycine (100 µg/ml, Sigma, St. Louis, USA, K-0245)) and the peptide MLDLQPETT in a concentration of 80 µg/ml.

4) Responder Cells

Responder cells are mononuclear peripheral blood lymphocytes (PBL) of a HLA-A2.1 subtyped donor (=C.B.). The PBL were separated from a buffy coat by Ficoll-procedure (Ficoll preparation: Lymphoprep of Nycomed-pharma, Oslo, Norway, cat.nr. 105033) and washed two times in RPMI. After separation and washing, the PBL were resuspended in complete RPMI medium with 30% human pooled serum (HPS) (HPS is tested for suppression activity in Mixed Lymphocyte Cultures).

5) Incubation of Primary Immune Response 400,000 PBL-C.B. in 50 µl of medium (the medium described in header 4) were added to each well of the 96-well-U-bottom plate already filled with T2 cells and cultured for 7 days at 37° C. in an incubator with 5% $CO_2$ and 90% humidity.

6) Restimulation (Day 7)

On day 7 after incubation of PBL, peptide MLDLQPETT (SEQ ID NO:15) and T2 cells (headers 1-5), the PBL-C.B. were restimulated with peptide MLDLQPETT (SEQ ID NO:15). For this purpose all cells and medium out of the 96 wells were harvested. Viable cells were isolated by Ficoll-procedure and washed in RPMI. In a new 96-well-U-bottom plate 50,000 of these viable cells were seeded to each well together with 50 µl complete RPMI medium with 15% HPS. Per well 20,000 autologous, irradiated (3000 rad) PBL and 50,000 autologous, irradiated (10000 rad) EBV-transformed B-lymphocytes (=EBV–C.B.) were added together with 50 µl of complete RPMI medium with 15% HPS and peptide MLDLQPETT (SEQ ID NO:15) in a concentration of 80 µg/ml. The cells were cultured for 7 days at 37° C. in an incubator with 5% $CO_2$ and 90% humidity.

7) Restimulation (Day 14)

On day 14 after incubation of PBL, peptide MLDLQPETT (SEQ ID NO:15) and T2 cells (headers 1-5), the PBL-C.B. were restimulated with peptide MLDLQPETT (SEQ ID NO:15). To do so the procedure under header 6 is repeated.

8) Cloning by Limiting Dilution

On day 21 after incubation of PBL, peptide MLDLQPE (SEQ ID NO:15) and T2 cells, cells and medium out of the 96 wells were harvested. Viable cells were isolated by Ficoll-procedure and washed in complete RPMI with 15% HPS. This bulk of viable cells was cloned by Limiting Dilution. Into each well of a new 96-well-U-bottom plate (Costar, Cambridge, USA, cat. nr. 3799) 50 µl complete RPMI medium with 15% HPS was added together with 100 viable cells (=HPV16 bulk anti MLDLQPETT (SEQ ID NO:15)). For other new 96-well-U-bottom plates this was exactly repeated except for the number of cells for wells: subsequent plates contained 10, 1, or 0.3 cells per well. To all wells 20,000 pooled and irradiated (3000 rad) PBL of four different donors and 10,000 pooled and irradiated (10,000 rad) EBV-transformed B-cells of three different HLA-A2.1 donors (VU-4/518/JY) were added together with 50 µl of complete RPMI medium with 15% HPS and peptide MLDLQPET (SEQ ID NO:15) in a concentration of 40 µg/ml, Leucoagglutinin in a concentration of 2% (Pharmacia, Uppsala, Sweden, cat.nr. 17-063-01), human recombinant IL-2 in a concentration of 120 IU/ml (Eurocetus, Amsterdam, The Netherlands).

9) Expand Clones

Add per well, in a final volume of 100 µl=>
25,000 viable cells
20,000 irradiated PBL-pool (as in header 8)
10,000 irradiated EBV-pool (as in header 8)
2 µg peptide MLDLQPETT (SEQ ID NO:15)
6 IU recombinant IL-2.

On day 49 a cytotoxicity assay was performed with 65 clones and one bulk as effector cells and T2 (with or without the relevant peptide MLDLQPETT (SEQ ID NO:15)) as target cells. Background killing is defined as killing of T2 cells incubated with an irrelevant (but HLA-A2.1 binding) peptide: ATELQTTIH (SEQ ID NO:75).

The HPV16 bulk (C.B.) anti MLDLQPETT (SEQ ID NO:15) seemed to be specific for killing MLDLQPETT (SEQ ID NO:15)-sensitized T2 cells. All the clones were not specific.

A new limiting dilution was done with the HPV16 bulk (C.B.) anti MLDLQPETT (SEQ ID NO:15) cells (as in header 8+9).

Figure 3:
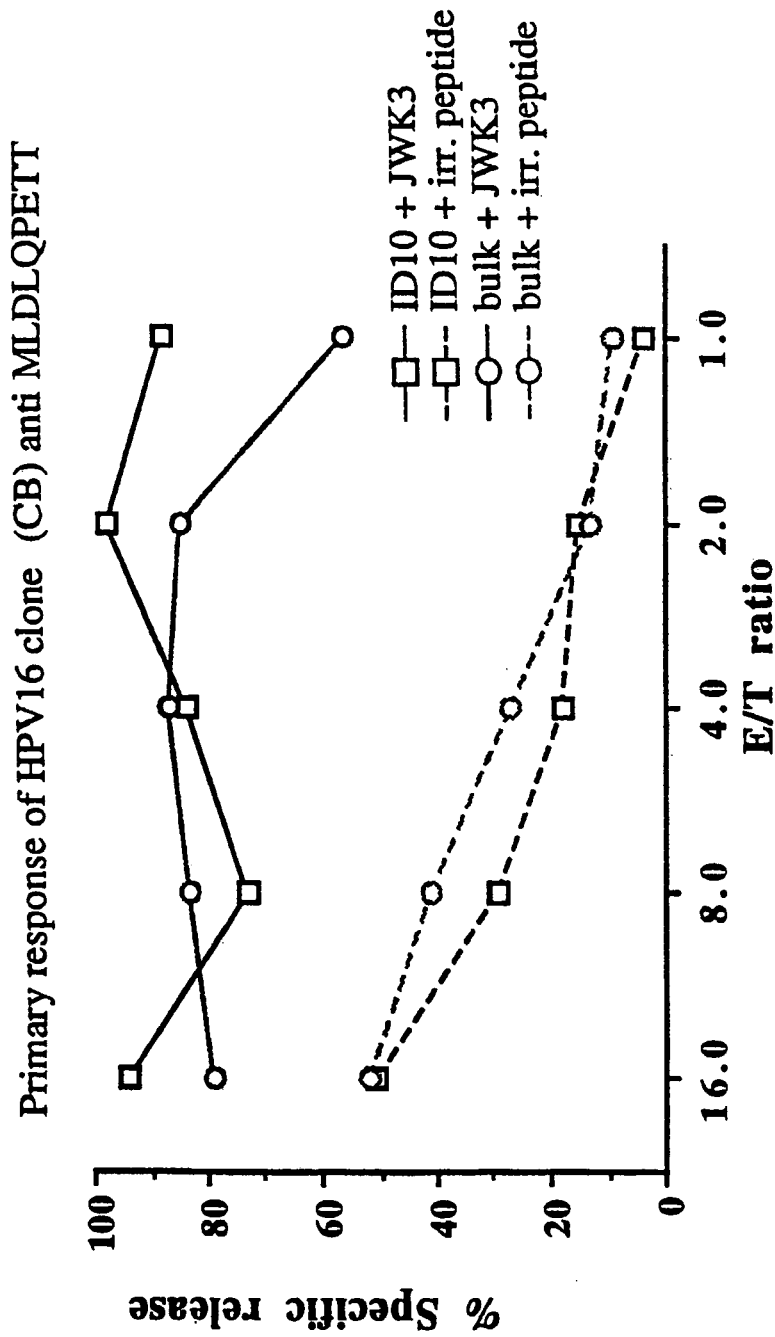
FIG. 3 is a graph showing the primary CTL response of human lymphocytes from healthy donor blood against an HPV16 peptide (peptide MLDLQPETT, No. 13 in Table I, SEQ ID NO 15). Bulk=bulk culture of CTL; clone=CTL clone from limiting dilution; irr. peptide=irrelevant peptide (control); and E/T ratio=effector target ratio.

On day 28 after the new limiting dilution a cytotoxicity assay was performed with five clones (ID10, ID12, ID19, ID26, ID92) and one bulk. A representative clone is shown in FIG. 3.

EXAMPLE 4

This example illustrates an immunochemical peptide-MHC binding assay which was used to determine which HPV16 protein E6 and E7 peptides bind to HLA-A1, A2.1, A3.2, A11.2 and A24 molecules.

The method utilizes purified class I molecules and radiolabeled synthetic probes based on consensus peptides. Competitor peptides tested for their binding to the class I molecules compete for this binding with the radiolabeled consensus peptides. The HLA-A1, A2.1, A3.2, A11.2, and A24 molecules were isolated from the following cell lines, respectively: the EBV (Eppstein Barr Virus) transformed cell line Steinlin, the EBV transformed cell line JY, the EBV transformed cell line GM3107, the cell line BVR and the EBV transformed cell line KT3. After large scale culture, cells were lysed in NP40 (Fluka Biochemika, Buchs, Switzerland) and the lysate was passed over two pre-columns of inactivated sepharose CL 4B and Prot A Sepharose. Class I molecules were then purified from the cell lysate by affinity chromatography using Prot A Sepharose beads conjugated with B2.23.2 (anti-HLA-B and HLA-C) and anti-human HLA. The lysate was first depleted of B and C molecules by repeated passage over the B2.23.2 column. Remaining HLA-A molecules were then captured by the W6/32 column and eluted by pH 11.5 DEA/1% OG neutralized with 1 mM Tris pH 6.8 and concentrated by ultrafiltration on Amicon 30 $K_D$ cartridges.

For binding assays, MHC amounts that resulted in binding of 15% of the radiolabeled synthetic probes (normally in the 10-50 nM range) were incubated in 0.05% NP40-PBS with about 5 nM of radiolabeled peptides and titrated amounts of unlabeled competitor peptides to be tested (usually in the 10 mg to 1 ng/ml range) in the presence of 1

µM β2M and a cocktail of protease inhibitors (with final concentrations of 1 mM PMSF, 1.3 mM 1,10-Phenanthroline, 73 µM Pepstatin A, 8 mM EDTA, 200 µM N-α-p-tosyl-L-Lysine Chloromethyl ketone). After two days at 23° C. the percent of MHC-bound radioactivity was measured by size exclusion chromatography on a TSK2000 gel filtration as described by Sette et al. (1992).

Probe peptides were iodinated by using the Chloramine T method described by Buus et al. (1987). The sequences of the probe peptides used for the aforementioned HLA molecules were YLEPAIAKY (SEQ ID NO:76) for A1, FLPSDYFPSV (SEQ ID NO:77) for A2.1, KVFPYALINK (SEQ ID NO:78) for A3.2, AVDLYHFLK (SEQ ID NO:79) for A11.2, and AYIDNYNKF (SEQ ID NO:80) for A24.

To allow comparison of the data obtained in different experiments, a relative binding figure was calculated for each peptide by dividing the 50% inhibition dose ($IC_{50}$) for the positive control for inhibition of unlabeled probe peptides by the 50% inhibition doses for each tested peptide. The values of the 50% inhibition dose for the probes was: 81 nM for A1, 5 nM for A2.1, 30 nM for A3.2, 9 nM for A11.2 and 22 nM for A24.

Each competitor peptide was tested in two to four completely independent experiments. Since cysteine containing peptides are susceptible to (air) oxidation during synthesis and handling, these peptides were synthesized with an alanine instead of a cysteine. Arbitrarily, the competitor peptides were categorized as good binders, intermediate binders, weak binders and negative binders when they fell into the following ratio categories: 1.0-0.1, 0.1-0.01, 0.01-0.001, and <0.001, respectively.

The results are shown in Tables IX to XIII.

TABLE IX

HPV16 E6 and E7 peptides binding to HLA-A1 in immunochemical assay

| Peptide | protein (region) | SEQ ID NO | binding ratio to standard# |
|---|---|---|---|
| YRDGNPYAV | E6 (residues 61-69) | 35 | 0.008 |
| WTGRCMSCC | E6 (residues 139-147) | 36 | 0.020 |
| MSCCRSSRT | E6 (residues 144-152) | 37 | 0.019 |
| TTDLYCYEQ | E7 (residues 19-27) | 38 | 0.023 |
| EIDGPAGQA | E7 (residues 37-45) | 39 | 0.025 |
| HVDIRTLED | E7 (residues 73-81) | 40 | 0.014 |

The average $IC_{50}$ value ± SE of the standard in the course of the experiments considered in this table was 81 ± 30 nM.

TABLE X

Additional HPV16 E6 and E7 peptides binding to HLA-A2.1 in immunochemical assay

| Peptide | protein (region) | SEQ ID NO | binding ratio to standard# |
|---|---|---|---|
| AMFQDPQER | E6 (residues 7-15) | 1 | 0.0033 |
| FAFRDLCIV | E6 (residues 52-60) | 10 | 0.3700 |

The average $IC_{50}$ value ± SE of the standard in the course of the experiments considered in this table was 6 ± 1 nM.

TABLE XI

HPV16 E6 and E7 peptides binding to HLA-A3.2 in immunochemical assay

| Peptide | protein (region) | SEQ ID NO | binding ratio to standard# |
|---|---|---|---|
| AMFQDPQER | E6 (residues 7-15) | 1 | 0.1000 |
| IILECVYCK | E6 (residues 33-41) | 41 | 1.5000 |
| CVYCKQQLL | E6 (residues 37-45) | 9 | 0.0320 |
| VYCKQQLLR | E6 (residues 38-46) | 42 | 0.0012 |
| QQLLRREVY | E6 (residues 42-50) | 43 | 0.0058 |
| IVYRDGNPY | E6 (residues 59-67) | 44 | 3.0000 |
| YAVCDKCLK | E6 (residues 67-75) | 45 | 0.0012 |
| AVCDKCLKF | E6 (residues 68-76) | 46 | 0.0056 |
| VCDKCLKFY | E6 (residues 69-77) | 47 | 0.0025 |
| KFYSKISEY | E6 (residues 75-83) | 48 | 0.0100 |
| KISEYRHYC | E6 (residues 79-87) | 11 | 0.0044 |
| ISEYRHYCY | E6 (residues 80-88) | 49 | 0.0064 |
| RHYCYSLYG | E6 (residues 84-92) | 50 | 0.0036 |
| SLYGTTLEQ | E6 (residues 89-97) | 51 | 0.0080 |
| TTLEQQYNK | E6 (residues 93-101) | 52 | 0.0780 |
| QQYNKPLCD | E6 (residues 97-105) | 53 | 0.0045 |
| LIRCINCQK | E6 (residues 107-115) | 54 | 3.7000 |
| HLDKKQRFH | E6 (residues 125-133) | 55 | 0.4400 |
| CMSCCRSSR | E6 (residues 143-151) | 56 | 0.1800 |
| SCCRSSRTR | E6 (residues 145-153) | 57 | 0.0200 |
| CCRSSRTRR | E6 (residues 146-154) | 58 | 0.0020 |
| HYNIVTFCC | E7 (residues 51-59) | 59 | 0.0260 |
| YNIVTFCCK | E7 (residues 52-60) | 60 | 0.0067 |
| CCKCDSTLR | E7 (residues 58-66) | 61 | 0.0016 |
| KCDSTLRLC | E7 (residues 60-68) | 62 | 0.0012 |

The average $IC_{50}$ value ± SE of the standard in the course of the experiments considered in this table was 30 ± 3 nM.

TABLE XII

HPV16 E6 and E7 peptides binding to HLA-A11.2 in immunochemical assay

| Peptide | protein (region) | SEQ ID NO | binding ratio to standard# |
|---|---|---|---|
| AMFQDPQER | E6 (residues 7-15) | 1 | 0.8400 |
| IILECVYCK | E6 (residues 33-41) | 41 | 6.7000 |
| CVYCKQQLL | E6 (residues 37-45) | 9 | 0.0450 |
| VYCKQQLLR | E6 (residues 38-46) | 42 | 0.0022 |
| QQLLRREVY | E6 (residues 42-50) | 43 | 0.0084 |
| IVYRDGNPY | E6 (residues 59-67) | 44 | 0.4700 |
| YAVCDKCLK | E6 (residues 67-75) | 45 | 0.0074 |
| AVCDKCLKF | E6 (residues 68-76) | 46 | 0.0037 |
| VCDKCLKFY | E6 (residues 69-77) | 47 | 0.0030 |
| KISEYRHYC | E6 (residues 79-87) | 11 | 0.0076 |
| ISEYRHYCY | E6 (residues 80-88) | 49 | 0.4300 |
| LIRCINCQK | E6 (residues 107-115) | 54 | 0.0120 |
| TGRCMSCCR | E6 (residues 140-148) | 63 | 0.0012 |
| CMSCCRSSR | E6 (residues 143-151) | 56 | 0.0084 |
| SCCRSSRTR | E6 (residues 145-153) | 57 | 0.0330 |
| HYNIVTFCC | E7 (residues 51-59) | 59 | 0.0010 |
| YNIVTFCCK | E7 (residues 52-60) | 60 | 0.0060 |
| CCKCDSTLR | E7 (residues 58-66) | 61 | 0.0110 |
| VCPICSQKP | E7 (residues 90-98) | 64 | 0.0012 |

The average $IC_{50}$ value ± SE of the standard in the course of the experiments considered in this table was 10 ± 3 nM.

TABLE XIII

HPV16 E6 and E7 peptides binding to HLA-A24 in immunochemical assay

| Peptide | protein (region) | SEQ ID NO | binding ratio to standard# |
|---|---|---|---|
| MHQKRTAMF | E6 (residues 1-9) | 65 | 0.0049 |
| LQTTIHDII | E6 (residues 26-34) | 6 | 0.0200 |

TABLE XIII-continued

HPV16 E6 and E7 peptides binding to HLA-A24 in immunochemical assay

| Peptide | protein (region) | SEQ ID NO | binding ratio to standard# |
|---|---|---|---|
| VYCKQQLLR | E6 (residues 38-46) | 42 | 0.0011 |
| LLRREVYDF | E6 (residues 44-52) | 66 | 0.0023 |
| VYDFAFRDL | E6 (residues 49-57) | 67 | 0.0610 |
| PYAVCDKCL | E6 (residues 66-74) | 68 | 0.0055 |
| KCLKFYSKI | E6 (residues 72-80) | 69 | 0.1100 |
| EYRHYCYSL | E6 (residues 82-90) | 70 | 0.0460 |
| HYCYSLYGT | E6 (residues 85-93) | 71 | 0.0037 |
| CYSLYGTTL | E6 (residues 87-95) | 72 | 0.1200 |
| RFHNIRGRW | E6 (residues 131-139) | 73 | 0.1000 |
| RAHYNIVTF | E7 (residues 49-57) | 74 | 0.0670 |

The average $IC_{50}$ value ± SE of the standard in the course of the experiments considered in this table was 22 ± 6 nM.

REFERENCES

1. W. M. Kast and C. J. M. Melief. In vivo efficacy of virus-derived peptides and virus-specific cytotoxic T lymphocytes. Immunology Letters 30: 229-232 (1991)
2. G. Reinholdsson-Ljunggren, T. Ramqvist, L. Ährlund-Richter and T. Dalianis. Int. J. Cancer 50: 142-146 (1992)
3. R. D. Salter and P. Cresswell. Impaired assembly and transport of HLA-A and -B antigens in a mutant T×B cell hybrid. EMBO J. 5: 943-949 (1986)
4. K. Seedorf, G. Krämmer, M. Dürst, S. Suhai and W. G. Röwekamp. Human Papillomavirus Type 16 DNA Sequence. Virology 145: 181-185 (1985)
5. W. R. Taylor. Identification of Protein Sequence Homology by Consensus Template Alignment. J. Mol. Biol. 188: 233-258 (1986)
6. H. Gausepohl and R. W. Frank. Automatische multiple Peptidsynthese. BioTec (September 1990)
7. H. Gausepohl, M. Kraft, C. Boulin and R. W. Frank. in: E. Giralt and D. Andreu (eds). Peptides 1990, 206-207 (1990)
8. W. Rapp, L. Zhang and E. Bayer. Continuous flow peptide synthesis on PSPOE-Graft-copolymers. In: Innovation and Perspectives in Solid Phase Peptide Synthesis, 205-210 (1990)
9. R. C. Sheppard and B. J. Williams. Acid-labile resin linkage agents for use in solid phase peptide synthesis. Int. J. Peptide Protein Res. 20, 451-454 (1982)
10. H. Gausepohl, M. Kraft and R. Frank. In situ activation of FMOC-amino acids by BOP in solid phase peptide synthesis. Peptides 1988, 241-243 (1988)
11. B. Castro, J. R. Dormoy, G. Evin and C. Selve. Reactifs de couplage peptidique IV (1)-L'hexafluorophosphate de benzotriazolyl N-oxytrisdimethylamino phosphonium (B.O.P.). Tetrahedron Letters 14: 1219-1222 (1975)
12. G. B. Fields and R. L. Noble. Solid phase peptide synthesis utilizing 9-fluorenylmethoxycarbonyl amino acids. Int. J. Peptide Protein Res. 35: 161-214 (1990)
13. A. Sette, S. Southwood, D. O'Sullivan, F. C. Gaeta, J. Sidney and H. M. Grey. Effect of pH on MHC class II-peptide interactions. J. Immunol. 148: 844 (1992)
14. S. Buus, A. Sette, S. M. Colon, C. Miles and H. M. Grey. The relation between major histocompatibility complex (MHC) restriction and the capacity of Ia to bind immunogenic peptides. Science 235: 1352 (1987)

The invention claimed is:

1. An isolated peptide comprising an amino acid sequence from 9 to 12 amino acids in length selected from the group consisting of:
AMFQDPQER (residues 7-15 of HPV16 protein E6) SEQ ID NO:1
KLPQLCTEL (residues 18-26 of HPV16 protein E6) SEQ ID NO:2
QLCTELQTT (residues 21-29 of HPV16 protein E6) SEQ ID NO:3
LCTELQTTI (residues 22-30 of HPV16 protein E6) SEQ ID NO:4
ELQTTIHDI (residues 25-33 of HPV16 protein E6) SEQ ID NO:5
LQTTIHDII (residues 26-34 of HPV16 protein E6) SEQ ID NO:6
TIHDIILEC (residues 29-37 of HPV16 protein E6) SEQ ID NO:7
IHDIILECV (residues 30-38 of HPV16 protein E6) SEQ ID NO:8
CVYCKQQLL (residues 37-45 of HPV16 protein E6) SEQ ID NO:9
FAFRDLCIV (residues 52-60 of HPV16 protein E6) SEQ ID NO:10
KISEYRHYC (residues 79-87 of HPV16 protein E6) SEQ ID NO:11
PLCDLLIRC (residues 102-110 of HPV16 protein E6) SEQ ID NO:12
TLHEYMLDL (residues 7-15 of HPV16 protein E7) SEQ ID NO:13
MLDLQPETT (residues 12-20 of HPV16 protein E7) SEQ ID NO:15
RLCVQSTHV (residues 66-74 of HPV16 protein E7) SEQ ID NO:16
TLEDLLMGT (residues 78-86 of HPV16 protein E7) SEQ ID NO:17
LLMGTLGIV (residues 82-90 of HPV16 protein E7) SEQ ID NO:18
GTLGIVCPI (residues 85-93 of HPV16 protein E7) SEQ ID NO:19 and
TLGIVCPIC (residues 86-94 of HPV16 protein E7) SEQ ID NO:20;
wherein said amino acid sequence is derived from protein E6 or E7 of HPV16; and
wherein said peptide has the ability to bind to human MHC Class I allele HLA-A2.1.

2. An isolated peptide comprising an amino acid sequence from 9 to 12 amino acids in length selected from the group consisting of:
KLPDLCTEL (residues 13-21 of HPV18 protein E6) SEQ ID NO:21
SLQDIEITC (residues 24-32 of HPV18 protein E6) SEQ ID NO:22
LQDIEITCV (residues 25-33 of HPV18 protein E6) SEQ ID NO:23
EITCVYCKT (residues 29-37 of HPV18 protein E6) SEQ ID NO:24
KTVLELTEV (residues 36-44 of HPV18 protein E6) SEQ ID NO:25
ELTEVFEFA (residues 40-48 of HPV18 protein E6) SEQ ID NO:26
FAFKDLFVV (residues 47-55 of HPV18 protein E6) SEQ ID NO:27
DTLEKLTNT (residues 88-96 of HPV18 protein E6) SEQ ID NO:28
LTNTGLYNL (residues 93-101 of HPV18 protein E6) SEQ ID NO:29
TLQDIVLHL (residues 7-15 of HPV18 protein E7) SEQ ID NO:30
FQQLFLNTL (residues 86-94 of HPV18 protein E7) SEQ ID NO:31
QLFLNTLSF (residues 88-96 of HPV18 protein E7) SEQ ID NO:32
LFLNTLSFV (residues 89-97 of HPV18 protein E7) SEQ ID NO:33 and
LSFVCPWCA (residues 94-102 of HPV18 protein E7) SEQ ID NO:34;
wherein said amino acid sequence is derived from protein E6 or E7 of HPV18; and
wherein said peptide has the ability to bind to human MHC Class I allele HLA-A2.1.

3. An isolated peptide comprising an amino acid sequence from 9 to 12 amino acids in length selected from the group consisting of:
YRDGNPYAV (residues 61-69 of HPV16 protein E6) SEQ ID NO:35
WTGRCMSCC (residues 139-147 of HPV16 protein E6) SEQ ID NO:36
MSCCRSSRT (residues 144-152 of HPV16 protein E6) SEQ ID NO:37
TTDLYCYEQ (residues 19-27 of HPV16 protein E7) SEQ ID NO:38
EIDGPAGQA (residues 37-45 of HPV16 protein E7) SEQ ID NO:39 and
HVDIRTLED (residues 73-81 of HPV16 protein E7) SEQ ID NO:40;
wherein said amino acid sequence is derived from protein E6 or E7 of HPV16; and
wherein said peptide has the ability to bind to human MHC Class I allele HLA-A1.

4. An isolated peptide comprising an amino acid sequence from 9 to 12 amino acids in length selected from the group consisting of:
AMFQDPQER (residues 7-15 of HPV16 protein E6) SEQ ID NO:1
IILECVYCK (residues 33-41 of HPV16 protein E6) SEQ ID NO:41
CVYCKQQLL (residues 37-45 of HPV16 protein E6) SEQ ID NO:9
VYCKQQLLR (residues 38-46 of HPV16 protein E6) SEQ ID NO:42
QQLLRREVY (residues 42-50 of HPV16 protein E6) SEQ ID NO:43
IVYRDGNPY (residues 59-67 of HPV16 protein E6) SEQ ID NO:44
YAVCDKCLK (residues 67-75 of HPV16 protein E6) SEQ ID NO:45
AVCDKCLKF (residues 68-76 of HPV16 protein E6) SEQ ID NO:46
VCDKCLKFY (residues 69-77 of HPV16 protein E6) SEQ ID NO:47
KFYSKISEY (residues 75-83 of HPV16 protein E6) SEQ ID NO:48
KISEYRHYC (residues 79-87 of HPV16 protein E6) SEQ ID NO:11
ISEYRHYCY (residues 80-88 of HPV16 protein E6) SEQ ID NO:49
RHYCYSLYG (residues 84-92 of HPV16 protein E6) SEQ ID NO:50
SLYGTTLEQ (residues 89-97 of HPV16 protein E6) SEQ ID NO:51
TTLEQQYNK (residues 93-101 of HPV16 protein E6) SEQ ID NO:52

QQYNKPLCD (residues 97-105 of HPV16 protein E6) SEQ ID NO:53
LIRCINCQK (residues 107-115 of HPV16 protein E6) SEQ ID NO:54
HLDKKQRFH (residues 125-133 of HPV16 protein E6) SEQ ID NO:55
CMSCCRSSR (residues 143-151 of HPV16 protein E6) SEQ ID NO:56
SCCRSSRTR (residues 145-153 of HPV16 protein E6) SEQ ID NO:57
CCRSSRTRR (residues 146-154 of HPV16 protein E6) SEQ ID NO:58
YNIVTFCCK (residues 52-60 of HPV16 protein E7) SEQ ID NO:60
CCKCDSTLR (residues 58-66 of HPV16 protein E7) SEQ ID NO:61 and
KCDSTLRLC (residues 60-68 of HPV16 protein E7) SEQ ID NO:62;

wherein said amino acid sequence is derived from protein E6 or E7 of HPV16; and
wherein said peptide has the ability to bind to human MHC Class I allele HLA-A3.2.

5. An isolated peptide comprising an amino acid sequence from 9 to 12 amino acids in length selected from the group consisting of:
AMFQDPQER (residues 7-15 of HPV16 protein E6) SEQ ID NO:1
IILECVYCK (residues 33-41 of HPV16 protein E6) SEQ ID NO:41
CVYCKQQLL (residues 37-45 of HPV16 protein E6) SEQ ID NO:9
VYCKQQLLR (residues 38-46 of HPV16 protein E6) SEQ ID NO:42
QQLLRREVY (residues 42-50 of HPV16 protein E6) SEQ ID NO:43
IVYRDGNPY (residues 59-67 of HPV16 protein E6) SEQ ID NO:44
YAVCDKCLK (residues 67-75 of HPV16 protein E6) SEQ ID NO:45
AVCDKCLKF (residues 68-76 of HPV16 protein E6) SEQ ID NO:46
VCDKCLKFY (residues 69-77 of HPV16 protein E6) SEQ ID NO:47
KISEYRHYC (residues 79-87 of HPV16 protein E6) SEQ ID NO:11
ISEYRHYCY (residues 80-88 of HPV16 protein E6) SEQ ID NO:49
LIRCINCQK (residues 107-115 of HPV16 protein E6) SEQ ID NO:54
TGRCMSCCR (residues 140-148 of HPV16 protein E6) SEQ ID NO:63
CMSCCRSSR (residues 143-151 of HPV16 protein E6) SEQ ID NO:56
SCCRSSRTR (residues 145-153 of HPV16 protein E6) SEQ ID NO:57
YNIVTFCCK (residues 52-60 of HPV16 protein E7) SEQ ID NO:60
CCKCDSTLR (residues 58-66 of HPV16 protein E7) SEQ ID NO:61 and
VCPICSQKP (residues 90-98 of HPV16 protein E7) SEQ ID NO:64;

wherein said amino acid sequence is derived from protein E6 or E7 of HPV16; and
wherein said peptide has the ability to bind to human MHC Class I allele HLA-A11.2.

6. An isolated peptide comprising an amino acid sequence from 9 to 12 amino acids in length selected from the group consisting of:
MHQKRTAMF (residues 1-9 of HPV16 protein E6) SEQ ID NO:65
LQTTIHDII (residues 26-34 of HPV16 protein E6) SEQ ID NO:6
VYCKQQLLR (residues 38-46 of HPV16 protein E6) SEQ ID NO:42
LLRREVYDF (residues 44-52 of HPV16 protein E6) SEQ ID NO:66
VYDFAFRDL (residues 49-57 of HPV16 protein E6) SEQ ID NO:67
PYAVCDKCL (residues 66-74 of HPV16 protein E6) SEQ ID NO:68
KCLKFYSKI (residues 72-80 of HPV16 protein E6) SEQ ID NO:69
EYRHYCYSL (residues 82-90 of HPV16 protein E6) SEQ ID NO:70
HYCYSLYGT (residues 85-93 of HPV16 protein E6) SEQ ID NO:71
CYSLYGTTL (residues 87-95 of HPV16 protein E6) SEQ ID NO:72
RFHNIRGRW (residues 131-139 of HPV16 protein E6) SEQ ID NO:73 and
RAHYNIVTF (residues 49-57 of HPV16 protein E7) SEQ ID NO:74;

wherein said amino acid sequence is derived from protein E6 or E7 of HPV16; and
wherein said peptide has the ability to bind to human MHC Class I allele HLA-A24.

7. A pharmaceutical composition comprising the peptide of claim 1 and a pharmaceutically acceptable carrier, diluent, excipient or adjuvant.

8. A pharmaceutical composition comprising the peptide of claim 2 and a pharmaceutically acceptable carrier, diluent, excipient or adjuvant.

9. A pharmaceutical composition comprising the peptide of claim 3 and a pharmaceutically acceptable carrier, diluent, excipient or adjuvant.

10. A pharmaceutical composition comprising the peptide of claim 4 and a pharmaceutically acceptable carrier, diluent, excipient or adjuvant.

11. A pharmaceutical composition comprising the peptide of claim 5 and a pharmaceutically acceptable carrier, diluent, excipient or adjuvant.

12. A pharmaceutical composition comprising the peptide of claim 6 and a pharmaceutically acceptable carrier, diluent, excipient or adjuvant.

* * * * *

```
                          SEQUENCE LISTING (1) GENERAL INFORMATION:

(iii) NUMBER OF SEQUENCES: 80

(2) INFORMATION FOR SEQ ID NO: 1:

(i) SEQUENCE CHARACTERISTICS:
        (A) LENGTH: 9 amino acids
        (B) TYPE: amino acid
        (C) STRANDEDNESS: unknown
        (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO: 1:

Ala Met Phe Gln Asp Pro Gln Glu Arg
1               5

(2) INFORMATION FOR SEQ ID NO: 2:

(i) SEQUENCE CHARACTERISTICS:
        (A) LENGTH: 9 amino acids
        (B) TYPE: amino acid
        (C) STRANDEDNESS: unknown
        (D) TOPOLOGY: unknown
```

```
        (ii) MOLECULE TYPE: peptide (iii) HYPOTHETICAL: NO (iv) ANTI-SENSE: NO (xi) SEQUENCE DESCRIPTION: SEQ ID NO: 2:

Lys Leu Pro Gln Leu Cys Thr Glu Leu
1               5

(2) INFORMATION FOR SEQ ID NO: 3:

(i) SEQUENCE CHARACTERISTICS:
            (A) LENGTH: 9 amino acids
            (B) TYPE: amino acid
            (C) STRANDEDNESS: unknown
            (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO: 3:

Gln Leu Cys Thr Glu Leu Gln Thr Thr
1               5

(2) INFORMATION FOR SEQ ID NO: 4:

(i) SEQUENCE CHARACTERISTICS:
            (A) LENGTH: 9 amino acids
            (B) TYPE: amino acid
            (C) STRANDEDNESS: unknown
            (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO: 4:

Leu Cys Thr Glu Leu Gln Thr Thr Ile
1               5

(2) INFORMATION FOR SEQ ID NO: 5:

(i) SEQUENCE CHARACTERISTICS:
            (A) LENGTH: 9 amino acids
            (B) TYPE: amino acid
            (C) STRANDEDNESS: unknown
            (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO: 5:

Glu Leu Gln Thr Thr Ile His Asp Ile
1               5

(2) INFORMATION FOR SEQ ID NO: 6:

(i) SEQUENCE CHARACTERISTICS:
            (A) LENGTH: 9 amino acids
            (B) TYPE: amino acid
            (C) STRANDEDNESS: unknown
```

(D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO: 6:

Leu Gln Thr Thr Ile His Asp Ile Ile
1               5

(2) INFORMATION FOR SEQ ID NO: 7:

(i) SEQUENCE CHARACTERISTICS:
        (A) LENGTH: 9 amino acids
        (B) TYPE: amino acid
        (C) STRANDEDNESS: unknown
        (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO: 7:

Thr Ile His Asp Ile Ile Leu Glu Cys
1               5

(2) INFORMATION FOR SEQ ID NO: 8:

(i) SEQUENCE CHARACTERISTICS:
        (A) LENGTH: 9 amino acids
        (B) TYPE: amino acid
        (C) STRANDEDNESS: unknown
        (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO: 8:

Ile His Asp Ile Ile Leu Glu Cys Val
1               5

(2) INFORMATION FOR SEQ ID NO: 9:

(i) SEQUENCE CHARACTERISTICS:
        (A) LENGTH: 9 amino acids
        (B) TYPE: amino acid
        (C) STRANDEDNESS: unknown
        (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO: 9:

Cys Val Tyr Cys Lys Gln Gln Leu Leu
1               5

(2) INFORMATION FOR SEQ ID NO: 10:

(i) SEQUENCE CHARACTERISTICS:
        (A) LENGTH: 9 amino acids
        (B) TYPE: amino acid

```
        (C) STRANDEDNESS: unknown
        (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO: 10:

Phe Ala Phe Arg Asp Leu Cys Ile Val
1               5

(2) INFORMATION FOR SEQ ID NO: 11:

(i) SEQUENCE CHARACTERISTICS:
        (A) LENGTH: 9 amino acids
        (B) TYPE: amino acid
        (C) STRANDEDNESS: unknown
        (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO: 11:

Lys Ile Ser Glu Tyr Arg His Tyr Cys
1               5

(2) INFORMATION FOR SEQ ID NO: 12:

(i) SEQUENCE CHARACTERISTICS:
        (A) LENGTH: 9 amino acids
        (B) TYPE: amino acid
        (C) STRANDEDNESS: unknown
        (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO: 12:

Pro Leu Cys Asp Leu Leu Ile Arg Cys
1               5

(2) INFORMATION FOR SEQ ID NO: 13:

(i) SEQUENCE CHARACTERISTICS:
        (A) LENGTH: 9 amino acids
        (B) TYPE: amino acid
        (C) STRANDEDNESS: unknown
        (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO: 13:

Thr Leu His Glu Tyr Met Leu Asp Leu
1               5

(2) INFORMATION FOR SEQ ID NO: 14:

(i) SEQUENCE CHARACTERISTICS:
        (A) LENGTH: 9 amino acids
```

```
        (B) TYPE: amino acid
        (C) STRANDEDNESS: unknown
        (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO: 14:

Tyr Met Leu Asp Leu Gln Pro Glu Thr
1               5

(2) INFORMATION FOR SEQ ID NO: 15:

(i) SEQUENCE CHARACTERISTICS:
        (A) LENGTH: 9 amino acids
        (B) TYPE: amino acid
        (C) STRANDEDNESS: unknown
        (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO: 15:

Met Leu Asp Leu Gln Pro Glu Thr Thr
1               5

(2) INFORMATION FOR SEQ ID NO: 16:

(i) SEQUENCE CHARACTERISTICS:
        (A) LENGTH: 9 amino acids
        (B) TYPE: amino acid
        (C) STRANDEDNESS: unknown
        (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO: 16:

Arg Leu Cys Val Gln Ser Thr His Val
1               5

(2) INFORMATION FOR SEQ ID NO: 17:

(i) SEQUENCE CHARACTERISTICS:
        (A) LENGTH: 9 amino acids
        (B) TYPE: amino acid
        (C) STRANDEDNESS: unknown
        (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO: 17:

Thr Leu Glu Asp Leu Leu Met Gly Thr
1               5

(2) INFORMATION FOR SEQ ID NO: 18:

(i) SEQUENCE CHARACTERISTICS:
```

```
            (A) LENGTH: 9 amino acids
            (B) TYPE: amino acid
            (C) STRANDEDNESS: unknown
            (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO: 18:

Leu Leu Met Gly Thr Leu Gly Ile Val
1               5

(2) INFORMATION FOR SEQ ID NO: 19:

(i) SEQUENCE CHARACTERISTICS:
            (A) LENGTH: 9 amino acids
            (B) TYPE: amino acid
            (C) STRANDEDNESS: unknown
            (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO: 19:

Gly Thr Leu Gly Ile Val Cys Pro Ile
1               5

(2) INFORMATION FOR SEQ ID NO: 20:

(i) SEQUENCE CHARACTERISTICS:
            (A) LENGTH: 9 amino acids
            (B) TYPE: amino acid
            (C) STRANDEDNESS: unknown
            (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO: 20:

Thr Leu Gly Ile Val Ala Pro Ile Cys
1               5

(2) INFORMATION FOR SEQ ID NO: 21:

(i) SEQUENCE CHARACTERISTICS:
            (A) LENGTH: 9 amino acids
            (B) TYPE: amino acid
            (C) STRANDEDNESS: unknown
            (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO: 21:

Lys Leu Pro Asp Leu Cys Thr Glu Leu
1               5

(2) INFORMATION FOR SEQ ID NO: 22:
```

(i) SEQUENCE CHARACTERISTICS:
            (A) LENGTH: 9 amino acids
            (B) TYPE: amino acid
            (C) STRANDEDNESS: unknown
            (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO: 22:

Ser Leu Gln Asp Ile Glu Ile Thr Cys
1               5

(2) INFORMATION FOR SEQ ID NO: 23:

(i) SEQUENCE CHARACTERISTICS:
            (A) LENGTH: 9 amino acids
            (B) TYPE: amino acid
            (C) STRANDEDNESS: unknown
            (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO: 23:

Leu Gln Asp Ile Glu Ile Thr Cys Val
1               5

(2) INFORMATION FOR SEQ ID NO: 24:

(i) SEQUENCE CHARACTERISTICS:
            (A) LENGTH: 9 amino acids
            (B) TYPE: amino acid
            (C) STRANDEDNESS: unknown
            (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO: 24:

Glu Ile Thr Cys Val Tyr Cys Lys Thr
1               5

(2) INFORMATION FOR SEQ ID NO: 25:

(i) SEQUENCE CHARACTERISTICS:
            (A) LENGTH: 9 amino acids
            (B) TYPE: amino acid
            (C) STRANDEDNESS: unknown
            (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO: 25:

Lys Thr Val Leu Glu Leu Thr Glu Val
1               5

(2) INFORMATION FOR SEQ ID NO: 26:

(i) SEQUENCE CHARACTERISTICS:
        (A) LENGTH: 9 amino acids
        (B) TYPE: amino acid
        (C) STRANDEDNESS: unknown
        (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO: 26:

Glu Leu Thr Glu Val Phe Glu Phe Ala
1               5

(2) INFORMATION FOR SEQ ID NO: 27:

(i) SEQUENCE CHARACTERISTICS:
        (A) LENGTH: 9 amino acids
        (B) TYPE: amino acid
        (C) STRANDEDNESS: unknown
        (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO: 27:

Phe Ala Phe Lys Asp Leu Phe Val Val
1               5

(2) INFORMATION FOR SEQ ID NO: 28:

(i) SEQUENCE CHARACTERISTICS:
        (A) LENGTH: 9 amino acids
        (B) TYPE: amino acid
        (C) STRANDEDNESS: unknown
        (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO: 28:

Asp Thr Leu Glu Lys Leu Thr Asn Thr
1               5

(2) INFORMATION FOR SEQ ID NO: 29:

(i) SEQUENCE CHARACTERISTICS:
        (A) LENGTH: 9 amino acids
        (B) TYPE: amino acid
        (C) STRANDEDNESS: unknown
        (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO: 29:

Leu Thr Asn Thr Gly Leu Tyr Asn Leu
1               5

-continued

```
(2) INFORMATION FOR SEQ ID NO: 30:

(i) SEQUENCE CHARACTERISTICS:
        (A) LENGTH: 9 amino acids
        (B) TYPE: amino acid
        (C) STRANDEDNESS: unknown
        (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO: 30:

Thr Leu Gln Asp Ile Val Leu His Leu
1               5

(2) INFORMATION FOR SEQ ID NO: 31:

(i) SEQUENCE CHARACTERISTICS:
        (A) LENGTH: 9 amino acids
        (B) TYPE: amino acid
        (C) STRANDEDNESS: unknown
        (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO: 31:

Phe Gln Gln Leu Phe Leu Asn Thr Leu
1               5

(2) INFORMATION FOR SEQ ID NO: 32:

(i) SEQUENCE CHARACTERISTICS:
        (A) LENGTH: 9 amino acids
        (B) TYPE: amino acid
        (C) STRANDEDNESS: unknown
        (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO: 32:

Gln Leu Phe Leu Asn Thr Leu Ser Phe
1               5

(2) INFORMATION FOR SEQ ID NO: 33:

(i) SEQUENCE CHARACTERISTICS:
        (A) LENGTH: 9 amino acids
        (B) TYPE: amino acid
        (C) STRANDEDNESS: unknown
        (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO: 33:

Leu Phe Leu Asn Thr Leu Ser Phe Val
1               5
```

(2) INFORMATION FOR SEQ ID NO: 34:

(i) SEQUENCE CHARACTERISTICS:
        (A) LENGTH: 9 amino acids
        (B) TYPE: amino acid
        (C) STRANDEDNESS: unknown
        (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO: 34:

Leu Ser Phe Val Cys Pro Trp Cys Ala
1               5

(2) INFORMATION FOR SEQ ID NO: 35:

(i) SEQUENCE CHARACTERISTICS:
        (A) LENGTH: 9 amino acids
        (B) TYPE: amino acid
        (C) STRANDEDNESS: unknown
        (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO: 35:

Tyr Arg Asp Gly Asn Pro Tyr Ala Val
1               5

(2) INFORMATION FOR SEQ ID NO: 36:

(i) SEQUENCE CHARACTERISTICS:
        (A) LENGTH: 9 amino acids
        (B) TYPE: amino acid
        (C) STRANDEDNESS: unknown
        (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO: 36:

Trp Thr Gly Arg Cys Met Ser Cys Cys
1               5

(2) INFORMATION FOR SEQ ID NO: 37:

(i) SEQUENCE CHARACTERISTICS:
        (A) LENGTH: 9 amino acids
        (B) TYPE: amino acid
        (C) STRANDEDNESS: unknown
        (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO: 37:

Met Ser Cys Cys Arg Ser Ser Arg Thr
1               5

-continued (2) INFORMATION FOR SEQ ID NO: 38:

(i) SEQUENCE CHARACTERISTICS:
        (A) LENGTH: 9 amino acids
        (B) TYPE: amino acid
        (C) STRANDEDNESS: unknown
        (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO: 38:

Thr Thr Asp Leu Tyr Cys Tyr Glu Gln
1            5

(2) INFORMATION FOR SEQ ID NO: 39:

(i) SEQUENCE CHARACTERISTICS:
        (A) LENGTH: 9 amino acids
        (B) TYPE: amino acid
        (C) STRANDEDNESS: unknown
        (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO: 39:

Glu Ile Asp Gly Pro Ala Gly Gln Ala
1            5

(2) INFORMATION FOR SEQ ID NO: 40:

(i) SEQUENCE CHARACTERISTICS:
        (A) LENGTH: 9 amino acids
        (B) TYPE: amino acid
        (C) STRANDEDNESS: unknown
        (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO: 40:

His Val Asp Ile Arg Thr Leu Glu Asp
1            5

(2) INFORMATION FOR SEQ ID NO: 41:

(i) SEQUENCE CHARACTERISTICS:
        (A) LENGTH: 9 amino acids
        (B) TYPE: amino acid
        (C) STRANDEDNESS: unknown
        (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO: 41:

Ile Ile Leu Glu Cys Val Tyr Cys Lys

-continued

```
1               5
```

(2) INFORMATION FOR SEQ ID NO: 42:

(i) SEQUENCE CHARACTERISTICS:
        (A) LENGTH: 9 amino acids
        (B) TYPE: amino acid
        (C) STRANDEDNESS: unknown
        (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO: 42:

```
Val Tyr Cys Lys Gln Gln Leu Leu Arg
1               5
```

(2) INFORMATION FOR SEQ ID NO: 43:

(i) SEQUENCE CHARACTERISTICS:
        (A) LENGTH: 9 amino acids
        (B) TYPE: amino acid
        (C) STRANDEDNESS: unknown
        (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO: 43:

```
Gln Gln Leu Leu Arg Arg Glu Val Tyr
1               5
```

(2) INFORMATION FOR SEQ ID NO: 44:

(i) SEQUENCE CHARACTERISTICS:
        (A) LENGTH: 9 amino acids
        (B) TYPE: amino acid
        (C) STRANDEDNESS: unknown
        (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO: 44:

```
Ile Val Tyr Arg Asp Gly Asn Pro Tyr
1               5
```

(2) INFORMATION FOR SEQ ID NO: 45:

(i) SEQUENCE CHARACTERISTICS:
        (A) LENGTH: 9 amino acids
        (B) TYPE: amino acid
        (C) STRANDEDNESS: unknown
        (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO: 45:

```
Tyr Ala Val Cys Asp Lys Cys Leu Lys
1               5
```

(2) INFORMATION FOR SEQ ID NO: 46:

(i) SEQUENCE CHARACTERISTICS:
        (A) LENGTH: 9 amino acids
        (B) TYPE: amino acid
        (C) STRANDEDNESS: unknown
        (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO: 46:

```
Ala Val Cys Asp Lys Cys Leu Lys Phe
1               5
```

(2) INFORMATION FOR SEQ ID NO: 47:

(i) SEQUENCE CHARACTERISTICS:
        (A) LENGTH: 9 amino acids
        (B) TYPE: amino acid
        (C) STRANDEDNESS: unknown
        (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO: 47:

```
Val Cys Asp Lys Cys Leu Lys Phe Tyr
1               5
```

(2) INFORMATION FOR SEQ ID NO: 48:

(i) SEQUENCE CHARACTERISTICS:
        (A) LENGTH: 9 amino acids
        (B) TYPE: amino acid
        (C) STRANDEDNESS: unknown
        (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO: 48:

```
Lys Phe Tyr Ser Lys Ile Ser Glu Tyr
1               5
```

(2) INFORMATION FOR SEQ ID NO: 49:

(i) SEQUENCE CHARACTERISTICS:
        (A) LENGTH: 9 amino acids
        (B) TYPE: amino acid
        (C) STRANDEDNESS: unknown
        (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO: 49:

```
Ile Ser Glu Tyr Arg His Tyr Cys Tyr
1               5
```

(2) INFORMATION FOR SEQ ID NO: 50:

(i) SEQUENCE CHARACTERISTICS:
        (A) LENGTH: 9 amino acids
        (B) TYPE: amino acid
        (C) STRANDEDNESS: unknown
        (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO: 50:

```
Arg His Tyr Cys Tyr Ser Leu Tyr Gly
1               5
```

(2) INFORMATION FOR SEQ ID NO: 51:

(i) SEQUENCE CHARACTERISTICS:
        (A) LENGTH: 9 amino acids
        (B) TYPE: amino acid
        (C) STRANDEDNESS: unknown
        (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO: 51:

```
Ser Leu Tyr Gly Thr Thr Leu Glu Gln
1               5
```

(2) INFORMATION FOR SEQ ID NO: 52:

(i) SEQUENCE CHARACTERISTICS:
        (A) LENGTH: 9 amino acids
        (B) TYPE: amino acid
        (C) STRANDEDNESS: unknown
        (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO: 52:

```
Thr Thr Leu Glu Gln Gln Tyr Asn Lys
1               5
```

(2) INFORMATION FOR SEQ ID NO: 53:

(i) SEQUENCE CHARACTERISTICS:
        (A) LENGTH: 9 amino acids
        (B) TYPE: amino acid
        (C) STRANDEDNESS: unknown
        (D) TOPOLOGY: unknown (ii) MOLECULE TYPE: peptide (iii) HYPOTHETICAL: NO (iv) ANTI-SENSE: NO -continued (xi) SEQUENCE DESCRIPTION: SEQ ID NO: 53:

Gln Gln Tyr Asn Lys Pro Leu Cys Asp
1               5

(2) INFORMATION FOR SEQ ID NO: 54:

(i) SEQUENCE CHARACTERISTICS:
            (A) LENGTH: 9 amino acids
            (B) TYPE: amino acid
            (C) STRANDEDNESS: unknown
            (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO: 54:

Leu Ile Arg Cys Ile Asn Cys Gln Lys
1               5

(2) INFORMATION FOR SEQ ID NO: 55:

(i) SEQUENCE CHARACTERISTICS:
            (A) LENGTH: 9 amino acids
            (B) TYPE: amino acid
            (C) STRANDEDNESS: unknown
            (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO: 55:

His Leu Asp Lys Lys Gln Arg Phe His
1               5

(2) INFORMATION FOR SEQ ID NO: 56:

(i) SEQUENCE CHARACTERISTICS:
            (A) LENGTH: 9 amino acids
            (B) TYPE: amino acid
            (C) STRANDEDNESS: unknown
            (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO: 56:

Cys Met Ser Cys Cys Arg Ser Ser Arg
1               5

(2) INFORMATION FOR SEQ ID NO: 57:

(i) SEQUENCE CHARACTERISTICS:
            (A) LENGTH: 9 amino acids
            (B) TYPE: amino acid
            (C) STRANDEDNESS: unknown
            (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO: 57:

Ser Cys Cys Arg Ser Ser Arg Thr Arg
1               5

(2) INFORMATION FOR SEQ ID NO: 58:

(i) SEQUENCE CHARACTERISTICS:
        (A) LENGTH: 9 amino acids
        (B) TYPE: amino acid
        (C) STRANDEDNESS: unknown
        (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO: 58:

Cys Cys Arg Ser Ser Arg Thr Arg Arg
1               5

(2) INFORMATION FOR SEQ ID NO: 59:

(i) SEQUENCE CHARACTERISTICS:
        (A) LENGTH: 9 amino acids
        (B) TYPE: amino acid
        (C) STRANDEDNESS: unknown
        (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO: 59:

His Tyr Asn Ile Val Thr Phe Cys Cys
1               5

(2) INFORMATION FOR SEQ ID NO: 60:

(i) SEQUENCE CHARACTERISTICS:
        (A) LENGTH: 9 amino acids
        (B) TYPE: amino acid
        (C) STRANDEDNESS: unknown
        (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO: 60:

Tyr Asn Ile Val Thr Phe Cys Cys Lys
1               5

(2) INFORMATION FOR SEQ ID NO: 61:

(i) SEQUENCE CHARACTERISTICS:
        (A) LENGTH: 9 amino acids
        (B) TYPE: amino acid
        (C) STRANDEDNESS: unknown
        (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO: 61:

Cys Cys Lys Cys Asp Ser Thr Leu Arg
1               5

(2) INFORMATION FOR SEQ ID NO: 62:

(i) SEQUENCE CHARACTERISTICS:
            (A) LENGTH: 9 amino acids
            (B) TYPE: amino acid
            (C) STRANDEDNESS: unknown
            (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO: 62:

Lys Cys Asp Ser Thr Leu Arg Leu Cys
1               5

(2) INFORMATION FOR SEQ ID NO: 63:

(i) SEQUENCE CHARACTERISTICS:
            (A) LENGTH: 9 amino acids
            (B) TYPE: amino acid
            (C) STRANDEDNESS: unknown
            (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO: 63:

Thr Gly Arg Cys Met Ser Cys Cys Arg
1               5

(2) INFORMATION FOR SEQ ID NO: 64:

(i) SEQUENCE CHARACTERISTICS:
            (A) LENGTH: 9 amino acids
            (B) TYPE: amino acid
            (C) STRANDEDNESS: unknown
            (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO: 64:

Val Cys Pro Ile Cys Ser Gln Lys Pro
1               5

(2) INFORMATION FOR SEQ ID NO: 65:

(i) SEQUENCE CHARACTERISTICS:
            (A) LENGTH: 9 amino acids
            (B) TYPE: amino acid
            (C) STRANDEDNESS: unknown
            (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO: 65:

Met His Gln Lys Arg Thr Ala Met Phe
1               5

(2) INFORMATION FOR SEQ ID NO: 66:

(i) SEQUENCE CHARACTERISTICS:
            (A) LENGTH: 9 amino acids
            (B) TYPE: amino acid
            (C) STRANDEDNESS: unknown
            (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO: 66:

Leu Leu Arg Arg Glu Val Tyr Asp Phe
1               5

(2) INFORMATION FOR SEQ ID NO: 67:

(i) SEQUENCE CHARACTERISTICS:
            (A) LENGTH: 9 amino acids
            (B) TYPE: amino acid
            (C) STRANDEDNESS: unknown
            (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO: 67:

Val Tyr Asp Phe Ala Phe Arg Asp Leu
1               5

(2) INFORMATION FOR SEQ ID NO: 68:

(i) SEQUENCE CHARACTERISTICS:
            (A) LENGTH: 9 amino acids
            (B) TYPE: amino acid
            (C) STRANDEDNESS: unknown
            (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO: 68:

Pro Tyr Ala Val Cys Asp Lys Cys Leu
1               5

(2) INFORMATION FOR SEQ ID NO: 69:

(i) SEQUENCE CHARACTERISTICS:
            (A) LENGTH: 9 amino acids
            (B) TYPE: amino acid
            (C) STRANDEDNESS: unknown
            (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO: 69:

Lys Cys Leu Lys Phe Tyr Ser Lys Ile
1               5

(2) INFORMATION FOR SEQ ID NO: 70:

(i) SEQUENCE CHARACTERISTICS:
         (A) LENGTH: 9 amino acids
         (B) TYPE: amino acid
         (C) STRANDEDNESS: unknown
         (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO: 70:

Glu Tyr Arg His Tyr Cys Tyr Ser Leu
1               5

(2) INFORMATION FOR SEQ ID NO: 71:

(i) SEQUENCE CHARACTERISTICS:
         (A) LENGTH: 9 amino acids
         (B) TYPE: amino acid
         (C) STRANDEDNESS: unknown
         (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO: 71:

His Tyr Cys Tyr Ser Leu Tyr Gly Thr
1               5

(2) INFORMATION FOR SEQ ID NO: 72:

(i) SEQUENCE CHARACTERISTICS:
         (A) LENGTH: 9 amino acids
         (B) TYPE: amino acid
         (C) STRANDEDNESS: unknown
         (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO: 72:

Cys Tyr Ser Leu Tyr Gly Thr Thr Leu
1               5

(2) INFORMATION FOR SEQ ID NO: 73:

(i) SEQUENCE CHARACTERISTICS:
         (A) LENGTH: 9 amino acids
         (B) TYPE: amino acid
         (C) STRANDEDNESS: unknown
         (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO: 73:

Arg Phe His Asn Ile Arg Gly Arg Trp
1               5

(2) INFORMATION FOR SEQ ID NO: 74:

(i) SEQUENCE CHARACTERISTICS:
            (A) LENGTH: 9 amino acids
            (B) TYPE: amino acid
            (C) STRANDEDNESS: unknown
            (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO: 74:

Arg Ala His Tyr Asn Ile Val Thr Phe
1               5

(2) INFORMATION FOR SEQ ID NO: 75:

(i) SEQUENCE CHARACTERISTICS:
            (A) LENGTH: 9 amino acids
            (B) TYPE: amino acid
            (C) STRANDEDNESS: unknown
            (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO: 75:

Ala Thr Glu Leu Gln Thr Thr Ile His
1               5

(2) INFORMATION FOR SEQ ID NO: 76:

(i) SEQUENCE CHARACTERISTICS:
            (A) LENGTH: 9 amino acids
            (B) TYPE: amino acid
            (C) STRANDEDNESS: unknown
            (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO: 76:

Tyr Leu Glu Pro Ala Ile Ala Lys Tyr
1               5

(2) INFORMATION FOR SEQ ID NO: 77:

(i) SEQUENCE CHARACTERISTICS:
            (A) LENGTH: 10 amino acids
            (B) TYPE: amino acid
            (C) STRANDEDNESS: unknown
            (D) TOPOLOGY: unknown -continued (ii) MOLECULE TYPE: peptide (iii) HYPOTHETICAL: NO (iv) ANTI-SENSE: NO (xi) SEQUENCE DESCRIPTION: SEQ ID NO: 77:

Phe Leu Pro Ser Asp Tyr Phe Pro Ser Val
1               5                   10

(2) INFORMATION FOR SEQ ID NO: 78:

(i) SEQUENCE CHARACTERISTICS:
            (A) LENGTH: 10 amino acids
            (B) TYPE: amino acid
            (C) STRANDEDNESS: unknown
            (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO: 78:

Lys Val Phe Pro Tyr Ala Leu Ile Asn Lys
1               5                   10

(2) INFORMATION FOR SEQ ID NO: 79:

(i) SEQUENCE CHARACTERISTICS:
            (A) LENGTH: 9 amino acids
            (B) TYPE: amino acid
            (C) STRANDEDNESS: unknown
            (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO: 79:

Ala Val Asp Leu Tyr His Phe Leu Lys
1               5

(2) INFORMATION FOR SEQ ID NO: 80:

(i) SEQUENCE CHARACTERISTICS:
            (A) LENGTH: 9 amino acids
            (B) TYPE: amino acid
            (C) STRANDEDNESS: unknown
            (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO: 80:

Ala Tyr Ile Asp Asn Tyr Asn Lys Phe
1               5